(12) United States Patent
Vanderveen et al.

(10) Patent No.: US 11,823,791 B2
(45) Date of Patent: Nov. 21, 2023

(54) CONTEXT-AWARE HEALTHCARE NOTIFICATION SYSTEM

(71) Applicant: CareFusion 303, Inc., San Diego, CA (US)

(72) Inventors: Timothy W. Vanderveen, Poway, CA (US); Federico Garibaldi, Encinitas, CA (US)

(73) Assignee: CAREFUSION 303, INC., San Diego, CA (US)

( * ) Notice: Subject to any disclaimer, the term of this patent is extended or adjusted under 35 U.S.C. 154(b) by 0 days.

(21) Appl. No.: 17/397,866

(22) Filed: Aug. 9, 2021

(65) Prior Publication Data

US 2021/0366600 A1    Nov. 25, 2021

Related U.S. Application Data

(63) Continuation of application No. 13/802,446, filed on Mar. 13, 2013, now Pat. No. 11,087,873, which is a
(Continued)

(51) Int. Cl.
*G16H 40/20* (2018.01)
*G06Q 10/00* (2023.01)
(Continued)

(52) U.S. Cl.
CPC .............. *G16H 40/20* (2018.01); *G06Q 10/00* (2013.01); *G06Q 10/10* (2013.01); *G16H 20/13* (2018.01);
(Continued)

(58) Field of Classification Search
CPC ......... G16H 40/20; G06Q 10/00; G06Q 10/10
See application file for complete search history.

(56) References Cited

U.S. PATENT DOCUMENTS 2,141,006 A    12/1938    Marinsky
3,724,455 A    4/1973    Unger
(Continued)

FOREIGN PATENT DOCUMENTS

CA    2472098    7/2003
CA    2554903    4/2005
(Continued)

OTHER PUBLICATIONS

Brazilian Office Action for Application No. BR112015029135-0, dated Aug. 30, 2022, 10 pages including translation.
(Continued)

*Primary Examiner* — Sheetal R Paulson
(74) *Attorney, Agent, or Firm* — Morgan, Lewis & Bockius LLP

(57) ABSTRACT

A context-aware healthcare notification system determines, in response to a user device has moved within a proximity of an infusion device and within a proximity of a patient identification device associated with a patient, that the infusion pump is currently experiencing an error condition regarding an administration of medication by the infusion pump to the patient. A corrective action is determined for the error condition and a notification is provided to the user device indicating that the user device is within the proximity of the infusion device and that the infusion device is experiencing the error condition, and information regarding the corrective action. The infusion device may then be caused to adjust the administration of medication by the infusion pump to the patient.

20 Claims, 11 Drawing Sheets

Related U.S. Application Data continuation-in-part of application No. 09/860,865, filed on May 18, 2001, now Pat. No. 9,600,633, said application No. 13/802,446 is a continuation-in-part of application No. 10/361,704, filed on Feb. 9, 2003, now abandoned, and a continuation-in-part of application No. 10/750,032, filed on Dec. 31, 2003, now abandoned, and a continuation-in-part of application No. 13/246,782, filed on Sep. 27, 2011, now abandoned, which is a continuation of application No. 12/947,773, filed on Nov. 16, 2010, now Pat. No. 8,340,792, which is a continuation of application No. 10/925,511, filed on Aug. 25, 2004, now Pat. No. 7,860,583, said application No. 13/802,446 is a continuation-in-part of application No. 11/326,145, filed on Dec. 30, 2005, now Pat. No. 9,427,520.

(60) Provisional application No. 60/205,125, filed on May 18, 2000, provisional application No. 60/652,382, filed on Feb. 11, 2005.

(51) Int. Cl.
*G06Q 10/10* (2023.01)
*G16H 20/13* (2018.01)
*G16H 20/17* (2018.01)
*G16H 40/63* (2018.01)
*G16H 40/67* (2018.01)
*G16H 70/60* (2018.01)

(52) U.S. Cl.
CPC ............. *G16H 20/17* (2018.01); *G16H 40/63* (2018.01); *G16H 40/67* (2018.01); *G16H 70/60* (2018.01)

(56) References Cited

U.S. PATENT DOCUMENTS

| | | |
|---|---|---|
| 3,831,006 A | 8/1974 | Chaffin, III et al. |
| 3,848,112 A | 11/1974 | Weichselbaum et al. |
| 3,872,448 A | 3/1975 | Mitchell, Jr. |
| 3,898,984 A | 8/1975 | Mandel et al. |
| 3,910,260 A | 10/1975 | Sarnoff et al. |
| 3,921,196 A | 11/1975 | Patterson |
| 3,970,996 A | 7/1976 | Yasaka et al. |
| 4,051,522 A | 9/1977 | Healy et al. |
| 4,135,241 A | 1/1979 | Stanis et al. |
| 4,164,320 A | 8/1979 | Irazoqui et al. |
| 4,216,462 A | 8/1980 | McGrath et al. |
| 4,237,344 A | 12/1980 | Moore |
| 4,315,309 A | 2/1982 | Coli |
| 4,321,461 A | 3/1982 | Walter, Jr. et al. |
| 4,360,125 A | 11/1982 | Martindale et al. |
| 4,373,527 A | 2/1983 | Fischell |
| 4,476,381 A | 10/1984 | Rubin |
| 4,604,847 A | 8/1986 | Moulding, Jr. et al. |
| 4,636,950 A | 1/1987 | Caswell et al. |
| 4,674,652 A | 6/1987 | Aten et al. |
| 4,676,776 A | 6/1987 | Howson |
| 4,688,026 A | 8/1987 | Scribner et al. |
| 4,695,954 A | 9/1987 | Rose et al. |
| 4,696,671 A | 9/1987 | Epstein et al. |
| 4,731,726 A | 3/1988 | Allen, III |
| 4,733,364 A | 3/1988 | Yamagata |
| 4,741,732 A | 5/1988 | Crankshaw et al. |
| 4,756,706 A | 7/1988 | Kerns et al. |
| 4,778,449 A | 10/1988 | Weber et al. |
| 4,785,969 A | 11/1988 | McLaughlin |
| 4,803,625 A | 2/1989 | Fu et al. |
| 4,810,243 A | 3/1989 | Howson |
| 4,828,545 A | 5/1989 | Epstein et al. |
| 4,831,562 A | 5/1989 | McIntosh et al. |
| 4,835,372 A | 5/1989 | Gombrich et al. |
| 4,839,806 A | 6/1989 | Goldfischer et al. |
| 4,847,764 A | 7/1989 | Halvorson |
| 4,850,009 A | 7/1989 | Zook et al. |
| 4,853,521 A | 8/1989 | Claeys et al. |
| 4,855,909 A | 8/1989 | Vincent et al. |
| 4,857,713 A | 8/1989 | Brown |
| 4,857,716 A | 8/1989 | Gombrich et al. |
| 4,865,584 A | 9/1989 | Epstein et al. |
| 4,882,575 A | 11/1989 | Kawahara |
| 4,899,839 A | 2/1990 | Dessertine et al. |
| 4,916,441 A | 4/1990 | Gombrich et al. |
| 4,918,604 A | 4/1990 | Baum |
| 4,925,444 A | 5/1990 | Orkin et al. |
| 4,942,544 A | 7/1990 | McIntosh et al. |
| 4,950,246 A | 8/1990 | Muller |
| 4,967,928 A | 11/1990 | Carter |
| 4,970,669 A | 11/1990 | McIntosh et al. |
| 4,978,335 A | 12/1990 | Arthur, III |
| 5,001,630 A | 3/1991 | Wiltfong |
| 5,006,699 A | 4/1991 | Felkner et al. |
| 5,036,462 A | 7/1991 | Kaufman et al. |
| 5,036,852 A | 8/1991 | Leishman |
| 5,041,086 A | 8/1991 | Koenig et al. |
| 5,072,383 A | 12/1991 | Brimm et al. |
| 5,077,666 A | 12/1991 | Brimm et al. |
| 5,078,683 A | 1/1992 | Sancoff et al. |
| 5,088,056 A | 2/1992 | McIntosh et al. |
| 5,088,981 A | 2/1992 | Howson et al. |
| 5,100,380 A | 3/1992 | Epstein et al. |
| 5,126,957 A | 6/1992 | Kaufman et al. |
| 5,142,484 A | 8/1992 | Kaufman et al. |
| 5,153,416 A | 10/1992 | Neeley |
| 5,153,827 A | 10/1992 | Coutre et al. |
| 5,164,575 A | 11/1992 | Neeley et al. |
| 5,166,498 A | 11/1992 | Neeley |
| 5,171,977 A | 12/1992 | Morrison |
| 5,181,910 A | 1/1993 | Scanlon |
| 5,190,522 A | 3/1993 | Wojcicki et al. |
| 5,207,642 A | 5/1993 | Orkin et al. |
| 5,235,507 A | 8/1993 | Sackler et al. |
| 5,256,157 A | 10/1993 | Samiotes et al. |
| 5,258,906 A | 11/1993 | Kroll et al. |
| 5,265,010 A | 11/1993 | Evans-Paganelli et al. |
| 5,267,174 A | 11/1993 | Kaufman et al. |
| 5,291,399 A | 3/1994 | Chaco |
| 5,292,029 A | 3/1994 | Pearson |
| 5,307,263 A | 4/1994 | Brown |
| 5,312,334 A | 5/1994 | Hara et al. |
| 5,314,243 A | 5/1994 | McDonald et al. |
| 5,315,505 A | 5/1994 | Pratt et al. |
| 5,317,506 A | 5/1994 | Coutre et al. |
| H1324 H | 6/1994 | Dalke et al. |
| 5,331,547 A | 7/1994 | Laszlo |
| 5,356,378 A | 10/1994 | Doan |
| 5,367,555 A | 11/1994 | Isoyama |
| 5,368,554 A | 11/1994 | Nazarian et al. |
| 5,371,692 A | 12/1994 | Draeger et al. |
| 5,374,813 A | 12/1994 | Shipp |
| 5,376,070 A | 12/1994 | Purvis et al. |
| 5,378,231 A | 1/1995 | Johnson et al. |
| 5,382,232 A | 1/1995 | Hague et al. |
| 5,390,238 A | 2/1995 | Kirk et al. |
| 5,401,059 A | 3/1995 | Ferrario |
| 5,404,384 A | 4/1995 | Colburn et al. |
| 5,408,443 A | 4/1995 | Weinberger |
| 5,412,372 A | 5/1995 | Parkhurst et al. |
| 5,412,564 A | 5/1995 | Ecer |
| 5,416,695 A | 5/1995 | Stutman et al. |
| 5,456,691 A | 10/1995 | Snell |
| 5,460,605 A | 10/1995 | Tuttle et al. |
| 5,465,082 A | 11/1995 | Chaco |
| 5,472,614 A | 12/1995 | Rossi |
| 5,502,944 A | 4/1996 | Kraft et al. |
| 5,515,426 A | 5/1996 | Yacenda et al. |
| 5,522,798 A | 6/1996 | Johnson et al. |
| 5,533,079 A | 7/1996 | Colburn et al. |
| 5,536,084 A | 7/1996 | Curtis et al. |
| 5,538,006 A | 7/1996 | Heim et al. |
| 5,542,420 A | 8/1996 | Goldman et al. |

(56) References Cited

U.S. PATENT DOCUMENTS

| | | |
|---|---|---|
| 5,544,649 A | 8/1996 | David et al. |
| 5,544,661 A | 8/1996 | Davis et al. |
| 5,547,470 A | 8/1996 | Johnson et al. |
| 5,561,412 A | 10/1996 | Novak et al. |
| 5,562,232 A | 10/1996 | Pearson |
| 5,564,803 A | 10/1996 | McDonald et al. |
| 5,573,506 A | 11/1996 | Vasko |
| 5,582,593 A | 12/1996 | Hultman |
| 5,583,758 A | 12/1996 | McIlroy et al. |
| 5,592,374 A | 1/1997 | Fellagara et al. |
| 5,594,786 A | 1/1997 | Chaco |
| 5,597,995 A | 1/1997 | Williams et al. |
| 5,601,445 A | 2/1997 | Schipper et al. |
| 5,622,429 A | 4/1997 | Heinze |
| 5,628,309 A | 5/1997 | Brown |
| 5,630,710 A | 5/1997 | Tune et al. |
| 5,633,910 A | 5/1997 | Cohen |
| 5,643,212 A | 7/1997 | Coutre et al. |
| 5,644,778 A | 7/1997 | Burks et al. |
| 5,645,531 A | 7/1997 | Thompson et al. |
| 5,651,775 A | 7/1997 | Walker et al. |
| 5,655,118 A | 8/1997 | Heindel et al. |
| 5,657,236 A | 8/1997 | Conkright |
| 5,658,250 A | 8/1997 | Blomquist et al. |
| 5,672,154 A | 9/1997 | Sillen et al. |
| 5,681,285 A | 10/1997 | Ford et al. |
| 5,683,367 A | 11/1997 | Jordan et al. |
| 5,685,844 A | 11/1997 | Marttila |
| 5,689,229 A | 11/1997 | Chaco et al. |
| 5,692,640 A | 12/1997 | Caulfield et al. |
| 5,699,038 A | 12/1997 | Ulrich et al. |
| 5,700,998 A | 12/1997 | Palti |
| 5,703,786 A | 12/1997 | Conkright |
| 5,704,352 A | 1/1998 | Tremblay et al. |
| 5,710,551 A | 1/1998 | Ridgeway |
| 5,712,913 A | 1/1998 | Chaum |
| 5,713,856 A | 2/1998 | Eggers |
| 5,721,913 A | 2/1998 | Ackroff et al. |
| 5,733,259 A | 3/1998 | Valcke et al. |
| 5,737,539 A | 4/1998 | Edelson et al. |
| 5,738,102 A | 4/1998 | Lemelson |
| 5,752,235 A | 5/1998 | Kehr et al. |
| 5,758,095 A | 5/1998 | Albaum et al. |
| 5,758,096 A | 5/1998 | Barsky et al. |
| 5,760,704 A | 6/1998 | Barton et al. |
| 5,764,034 A | 6/1998 | Bowman et al. |
| 5,772,585 A | 6/1998 | Lavin et al. |
| 5,774,865 A | 6/1998 | Glynn |
| 5,781,442 A | 7/1998 | Engelson et al. |
| 5,790,409 A | 8/1998 | Fedor et al. |
| 5,795,327 A | 8/1998 | Wilson et al. |
| 5,803,906 A | 9/1998 | Pratt et al. |
| 5,807,321 A | 9/1998 | Stoker et al. |
| 5,807,336 A | 9/1998 | Russo et al. |
| 5,819,229 A | 10/1998 | Boppe |
| 5,822,418 A | 10/1998 | Yacenda et al. |
| 5,822,544 A | 10/1998 | Chaco et al. |
| 5,832,488 A | 11/1998 | Eberhardt |
| 5,833,599 A | 11/1998 | Schrier et al. |
| 5,842,173 A | 11/1998 | Strum et al. |
| 5,842,976 A | 12/1998 | Williamson |
| 5,845,253 A | 12/1998 | Rensimer et al. |
| 5,845,254 A | 12/1998 | Lockwood et al. |
| 5,845,255 A | 12/1998 | Mayaud |
| 5,845,264 A | 12/1998 | Nellhaus |
| 5,848,593 A | 12/1998 | McGrady et al. |
| 5,850,344 A | 12/1998 | Conkright |
| 5,852,408 A | 12/1998 | Christiansen et al. |
| 5,855,550 A | 1/1999 | Lai et al. |
| 5,867,821 A | 2/1999 | Ballantyne et al. |
| 5,871,465 A | 2/1999 | Vasko |
| 5,883,806 A | 3/1999 | Meador et al. |
| 5,885,245 A | 3/1999 | Lynch et al. |
| 5,894,273 A | 4/1999 | Meador et al. |
| 5,895,371 A | 4/1999 | Levitas et al. |
| 5,985,371 A | 4/1999 | Fujioka et al. |
| 5,899,998 A | 5/1999 | McGauley et al. |
| 5,903,211 A | 5/1999 | Flego et al. |
| 5,905,653 A | 5/1999 | Higham et al. |
| 5,907,490 A | 5/1999 | Oliver |
| 5,911,132 A | 6/1999 | Sloane |
| 5,911,687 A | 6/1999 | Sato et al. |
| 5,912,818 A | 6/1999 | McGrady et al. |
| 5,920,054 A | 6/1999 | Uber, III |
| 5,920,263 A | 7/1999 | Huttenhoff et al. |
| 5,928,329 A | 7/1999 | Clark et al. |
| 5,930,145 A | 7/1999 | Yuyama et al. |
| 5,935,099 A | 8/1999 | Peterson et al. |
| 5,941,710 A | 8/1999 | Lampotang et al. |
| 5,942,986 A | 8/1999 | Shabot et al. |
| 5,950,630 A | 9/1999 | Portwood et al. |
| 5,950,632 A | 9/1999 | Reber et al. |
| 5,953,099 A | 9/1999 | Walach |
| 5,954,641 A | 9/1999 | Kehr et al. |
| 5,957,885 A | 9/1999 | Bollish et al. |
| 5,961,036 A | 10/1999 | Michael et al. |
| 5,961,446 A | 10/1999 | Beller et al. |
| 5,971,593 A | 10/1999 | McGrady |
| 5,995,077 A | 11/1999 | Wilcox et al. |
| 5,995,937 A | 11/1999 | DeBusk et al. |
| 6,000,828 A | 12/1999 | Leet |
| 6,003,006 A | 12/1999 | Colella et al. |
| 6,009,333 A | 12/1999 | Chaco |
| 6,017,318 A | 1/2000 | Gauthier et al. |
| 6,021,392 A | 2/2000 | Lester et al. |
| 6,024,699 A | 2/2000 | Surwit et al. |
| 6,032,155 A | 2/2000 | de la Huerga |
| 6,039,251 A | 3/2000 | Holowko et al. |
| 6,047,203 A | 4/2000 | Sackner et al. |
| 6,048,087 A | 4/2000 | Laurent et al. |
| 6,053,887 A | 4/2000 | Levitas et al. |
| 6,063,026 A | 5/2000 | Schauss et al. |
| 6,082,776 A | 7/2000 | Feinberg |
| 6,112,182 A | 8/2000 | Akers et al. |
| RE36,871 E | 9/2000 | Epstein et al. |
| 6,134,582 A | 10/2000 | Kennedy |
| 6,135,949 A | 10/2000 | Russo et al. |
| 6,202,923 B1 | 3/2001 | Boyer et al. |
| 6,228,057 B1 | 5/2001 | Vasko |
| 6,241,704 B1 | 6/2001 | Peterson et al. |
| 6,269,340 B1 | 7/2001 | Ford et al. |
| 6,282,441 B1 | 8/2001 | Raymond et al. |
| 6,290,681 B1 | 9/2001 | Brown |
| 6,292,698 B1 | 9/2001 | Duffin et al. |
| 6,302,844 B1 | 10/2001 | Walker et al. |
| 6,312,378 B1 | 11/2001 | Bardy |
| 6,314,556 B1 | 11/2001 | DeBusk et al. |
| 6,319,200 B1 | 11/2001 | Lai et al. |
| 6,322,502 B1 | 11/2001 | Schoenberg et al. |
| 6,338,007 B1 | 1/2002 | Broadfield et al. |
| 6,339,732 B1 | 1/2002 | Phoon et al. |
| 6,406,426 B1 | 6/2002 | Reuss et al. |
| 6,409,684 B1 | 6/2002 | Wilk |
| 6,421,650 B1 | 7/2002 | Goetz et al. |
| 6,493,747 B2 | 12/2002 | Simmon et al. |
| 6,519,569 B1 | 2/2003 | White et al. |
| 6,529,892 B1 | 3/2003 | Lambert |
| 6,540,672 B1 | 4/2003 | Simonsen et al. |
| 6,558,352 B1 | 5/2003 | Hogan |
| 6,571,128 B2 | 5/2003 | Lebel et al. |
| 6,581,606 B2 | 6/2003 | Kutzko et al. |
| 6,671,563 B1 | 12/2003 | Engelson et al. |
| 6,745,764 B2 | 6/2004 | Hickle |
| 6,757,898 B1 | 7/2004 | Ilsen et al. |
| 6,785,589 B2 | 8/2004 | Eggenberger et al. |
| 6,796,956 B2 | 9/2004 | Hartlaub et al. |
| 6,799,149 B2 | 9/2004 | Hartlaub |
| 6,847,861 B2 | 1/2005 | Lunak et al. |
| 6,856,247 B1 | 2/2005 | Wallace |
| 6,873,268 B2 | 3/2005 | Lebel et al. |
| 6,993,402 B2 | 1/2006 | Klass et al. |
| 7,034,691 B1 | 4/2006 | Rapaport et al. |
| 7,054,844 B2 | 5/2006 | Fletcher et al. |
| 7,060,059 B2 | 6/2006 | Keith et al. |

(56) References Cited

U.S. PATENT DOCUMENTS

| | | |
|---|---|---|
| 7,096,072 B2 | 8/2006 | Engleson et al. |
| 7,201,734 B2 | 4/2007 | Hickle |
| 7,204,823 B2 | 4/2007 | Estes et al. |
| 7,215,991 B2 | 5/2007 | Besson et al. |
| 7,229,430 B2 | 6/2007 | Hickle et al. |
| 7,230,529 B2 | 6/2007 | Ketcherside, Jr. et al. |
| 7,256,708 B2 | 8/2007 | Rosenfeld et al. |
| 7,263,492 B1 | 8/2007 | Suresh et al. |
| 7,379,885 B1 | 5/2008 | Zakim |
| 7,384,420 B2 | 6/2008 | Dycus et al. |
| 7,398,183 B2* | 7/2008 | Holland ............... G16H 40/67 702/182 |
| 7,421,709 B2 | 9/2008 | Watson et al. |
| 7,433,853 B2 | 10/2008 | Brockway et al. |
| 7,471,994 B2 | 12/2008 | Ford et al. |
| 7,526,769 B2 | 4/2009 | Watts, Jr. et al. |
| 7,587,415 B2 | 9/2009 | Guarav et al. |
| 7,612,679 B1 | 11/2009 | Fackler et al. |
| 7,693,697 B2 | 4/2010 | Westenskow et al. |
| 7,769,601 B1 | 8/2010 | Bleser et al. |
| 7,771,385 B2 | 8/2010 | Eggers et al. |
| 7,771,386 B2 | 8/2010 | Eggers et al. |
| 7,776,031 B2 | 8/2010 | Hartlaub et al. |
| 7,787,946 B2 | 8/2010 | Stahmann et al. |
| 7,796,045 B2 | 9/2010 | Spear et al. |
| 7,835,927 B2 | 11/2010 | Schlotterbeck et al. |
| 7,847,970 B1 | 12/2010 | McGrady |
| 7,860,583 B2 | 12/2010 | Condurso et al. |
| 7,962,544 B2 | 6/2011 | Torok et al. |
| 7,970,550 B2 | 6/2011 | Arakelyan et al. |
| 8,005,688 B2 | 8/2011 | Coffman et al. |
| 8,024,200 B2 | 9/2011 | Jennings et al. |
| 8,160,895 B2 | 4/2012 | Schmitt et al. |
| 8,197,437 B2 | 6/2012 | Kalafut et al. |
| 8,291,337 B2 | 10/2012 | Gannin et al. |
| 8,340,792 B2 | 12/2012 | Condurso et al. |
| 8,630,722 B2 | 1/2014 | Condurso et al. |
| 8,689,008 B2 | 4/2014 | Rangadass et al. |
| 8,761,906 B2 | 6/2014 | Condurso et al. |
| 10,192,193 B1 | 1/2019 | Glass |
| 10,417,758 B1 | 9/2019 | Alexander |
| 10,692,207 B2 | 6/2020 | Sandmann et al. |
| 2001/0037083 A1 | 11/2001 | Hartlaub et al. |
| 2001/0044731 A1 | 11/2001 | Coffman et al. |
| 2002/0010679 A1 | 1/2002 | Felsher |
| 2002/0016568 A1 | 2/2002 | Lebel et al. |
| 2002/0016923 A1 | 2/2002 | Knaus et al. |
| 2002/0022973 A1 | 2/2002 | Sun et al. |
| 2002/0026223 A1 | 2/2002 | Riff et al. |
| 2002/0035484 A1 | 3/2002 | McCormick |
| 2002/0038392 A1 | 3/2002 | De La Huerga |
| 2002/0042636 A1 | 4/2002 | Koshiol et al. |
| 2002/0046346 A1 | 4/2002 | Evans |
| 2002/0077849 A1 | 6/2002 | Baruch et al. |
| 2002/0087114 A1 | 7/2002 | Hartlaub |
| 2002/0116509 A1 | 8/2002 | De La Huerga |
| 2002/0120350 A1 | 8/2002 | Klass et al. |
| 2002/0169636 A1* | 11/2002 | Eggers ................. G16H 10/60 705/3 |
| 2002/0198624 A1 | 12/2002 | Greenwald et al. |
| 2003/0009244 A1 | 1/2003 | Engleson et al. |
| 2003/0036683 A1 | 2/2003 | Kehr et al. |
| 2003/0045858 A1 | 3/2003 | Struys et al. |
| 2003/0051737 A1 | 3/2003 | Hickle et al. |
| 2003/0063524 A1 | 4/2003 | Niemiec et al. |
| 2003/0069481 A1 | 4/2003 | Hervy et al. |
| 2003/0105389 A1 | 6/2003 | Noonan et al. |
| 2003/0105555 A1 | 6/2003 | Lunak et al. |
| 2003/0106553 A1 | 6/2003 | Vanderveen |
| 2003/0114836 A1 | 6/2003 | Estes et al. |
| 2003/0121517 A1 | 7/2003 | McFarland |
| 2003/0129578 A1 | 7/2003 | Mault |
| 2003/0135087 A1 | 7/2003 | Hickle et al. |
| 2003/0135388 A1 | 7/2003 | Martucci et al. |
| 2003/0139701 A1 | 7/2003 | White et al. |
| 2003/0140928 A1 | 7/2003 | Bui et al. |
| 2003/0140929 A1 | 7/2003 | Wilkes et al. |
| 2003/0149599 A1 | 8/2003 | Goodall et al. |
| 2003/0156143 A1 | 8/2003 | Westenskow et al. |
| 2003/0158746 A1 | 8/2003 | Forrester |
| 2003/0163223 A1 | 8/2003 | Blomguist |
| 2003/0205897 A1 | 11/2003 | Kaufman |
| 2003/0236683 A1 | 12/2003 | Henderson et al. |
| 2004/0068229 A1 | 4/2004 | Jansen et al. |
| 2004/0073329 A1 | 4/2004 | Engleson et al. |
| 2004/0107118 A1 | 6/2004 | Harnsberger et al. |
| 2004/0122702 A1 | 6/2004 | Sabol et al. |
| 2004/0122705 A1 | 6/2004 | Sabol et al. |
| 2004/0122719 A1 | 6/2004 | Sabol et al. |
| 2004/0122790 A1 | 6/2004 | Walker et al. |
| 2004/0128162 A1 | 7/2004 | Schlotterbeck et al. |
| 2004/0152622 A1 | 8/2004 | Keith et al. |
| 2004/0167465 A1 | 8/2004 | Mihai et al. |
| 2004/0167804 A1 | 8/2004 | Simpson et al. |
| 2004/0172283 A1 | 9/2004 | Vanderveen et al. |
| 2004/0172300 A1 | 9/2004 | Mihai et al. |
| 2004/0172302 A1 | 9/2004 | Martucci et al. |
| 2004/0176297 A1 | 9/2004 | Cheung et al. |
| 2004/0188998 A1 | 9/2004 | Henthorn |
| 2004/0193325 A1 | 9/2004 | Bonderud et al. |
| 2004/0193446 A1 | 9/2004 | Mayer et al. |
| 2004/0260478 A1 | 12/2004 | Schwamm |
| 2005/0010166 A1 | 1/2005 | Hickle |
| 2005/0010269 A1 | 1/2005 | Lebel et al. |
| 2005/0020996 A1 | 1/2005 | Hartlaub et al. |
| 2005/0021297 A1 | 1/2005 | Hartlaub |
| 2005/0022274 A1 | 1/2005 | Campbell et al. |
| 2005/0033606 A1 | 2/2005 | Miller |
| 2005/0049179 A1 | 3/2005 | Davidson et al. |
| 2005/0055242 A1 | 3/2005 | Bello et al. |
| 2005/0088296 A1 | 4/2005 | Lee |
| 2005/0096941 A1 | 5/2005 | Tong |
| 2005/0097566 A1 | 5/2005 | Watts et al. |
| 2005/0107914 A1 | 5/2005 | Engleson et al. |
| 2005/0108057 A1 | 5/2005 | Cohen et al. |
| 2005/0113945 A1 | 5/2005 | Engleson et al. |
| 2005/0119788 A1 | 6/2005 | Engleson et al. |
| 2005/0144043 A1 | 6/2005 | Holland et al. |
| 2005/0145010 A1 | 7/2005 | Vanderveen et al. |
| 2005/0148890 A1 | 7/2005 | Hastings |
| 2005/0171815 A1 | 8/2005 | Vanderveen |
| 2005/0224083 A1 | 10/2005 | Crass et al. |
| 2005/0278194 A1 | 12/2005 | Holland et al. |
| 2006/0026205 A1 | 2/2006 | Butterfield |
| 2006/0047538 A1 | 3/2006 | Condurso et al. |
| 2006/0053036 A1 | 3/2006 | Coffman et al. |
| 2006/0079831 A1 | 4/2006 | Gilbert |
| 2006/0101072 A1 | 5/2006 | Busche et al. |
| 2006/0122481 A1 | 6/2006 | Sievenpiper et al. |
| 2006/0190302 A1 | 8/2006 | Eggers et al. |
| 2006/0200369 A1 | 9/2006 | Batch et al. |
| 2006/0200356 A1 | 9/2006 | Vanderveen |
| 2006/0217628 A1 | 9/2006 | Huiku |
| 2006/0218015 A1 | 9/2006 | Walker et al. |
| 2006/0229551 A1 | 10/2006 | Martinez et al. |
| 2006/0249423 A1 | 11/2006 | Reijonen |
| 2006/0271401 A1 | 11/2006 | Lassetter et al. |
| 2006/0287890 A1 | 12/2006 | Stead et al. |
| 2007/0015972 A1 | 1/2007 | Wang et al. |
| 2007/0043767 A1 | 2/2007 | Osborne et al. |
| 2007/0061266 A1 | 3/2007 | Moore et al. |
| 2007/0061393 A1 | 3/2007 | Moore |
| 2007/0083389 A1 | 4/2007 | Dyer et al. |
| 2007/0106457 A1 | 5/2007 | Rosenberg |
| 2007/0106753 A1 | 5/2007 | Moore |
| 2007/0106754 A1 | 5/2007 | Moore |
| 2007/0129647 A1 | 6/2007 | Lynn |
| 2007/0156452 A1 | 7/2007 | Batch |
| 2007/0156860 A1 | 7/2007 | Nedelcu et al. |
| 2007/0168301 A1 | 7/2007 | Eisner et al. |
| 2007/0208454 A1 | 9/2007 | Forrester et al. |
| 2007/0210157 A1 | 9/2007 | Miller |
| 2007/0286466 A1 | 12/2007 | Heffernan et al. |
| 2007/0293843 A1 | 12/2007 | Ireland et al. |

(56) References Cited

U.S. PATENT DOCUMENTS

| | | |
|---|---|---|
| 2008/0015549 A1 | 1/2008 | Maughan |
| 2008/0025230 A1 | 1/2008 | Patel et al. |
| 2008/0034323 A1 | 2/2008 | Blomquist |
| 2008/0040151 A1 | 2/2008 | Moore |
| 2008/0046292 A1 | 2/2008 | Myers et al. |
| 2008/0141272 A1 | 6/2008 | Borgendale et al. |
| 2008/0162254 A1 | 7/2008 | Herger et al. |
| 2008/0164998 A1 | 7/2008 | Scherpbier et al. |
| 2008/0169045 A1 | 7/2008 | Tribble et al. |
| 2008/0195246 A1 | 8/2008 | Tribble et al. |
| 2008/0272138 A1 | 11/2008 | Ross et al. |
| 2008/0317672 A1 | 12/2008 | Viertio-Oja |
| 2009/0012812 A1 | 1/2009 | Rausch et al. |
| 2009/0012813 A1 | 1/2009 | Berzansky et al. |
| 2009/0043253 A1 | 2/2009 | Podaima |
| 2009/0054754 A1 | 2/2009 | McMahon et al. |
| 2009/0062727 A1 | 3/2009 | Woo |
| 2009/0099867 A1 | 4/2009 | Newman |
| 2009/0112333 A1 | 4/2009 | Sahai |
| 2009/0125335 A1 | 5/2009 | Manetta et al. |
| 2009/0150484 A1 | 6/2009 | Roberts |
| 2009/0210252 A1 | 8/2009 | Silver |
| 2009/0240651 A1 | 9/2009 | Fletcher et al. |
| 2009/0306585 A1 | 12/2009 | Pang et al. |
| 2009/0306944 A1 | 12/2009 | Willmann et al. |
| 2009/0319623 A1 | 12/2009 | Srinivasan et al. |
| 2010/0037067 A1 | 2/2010 | Rangadass et al. |
| 2010/0094653 A1 | 4/2010 | Tribble et al. |
| 2010/0121654 A1 | 5/2010 | Portnoy et al. |
| 2010/0161113 A1 | 6/2010 | Tribble et al. |
| 2010/0169120 A1 | 7/2010 | Herbst et al. |
| 2010/0169771 A1 | 7/2010 | Pelegrin et al. |
| 2010/0174552 A1 | 7/2010 | Hawkes et al. |
| 2010/0174553 A1 | 7/2010 | Kaufman et al. |
| 2010/0179825 A1 | 7/2010 | Hanov et al. |
| 2010/0241453 A1 | 9/2010 | Malec |
| 2010/0241456 A1 | 9/2010 | Miller et al. |
| 2010/0271218 A1 | 10/2010 | Hoag et al. |
| 2010/0280840 A1 | 11/2010 | Fukushi et al. |
| 2010/0323397 A1 | 12/2010 | Reavy et al. |
| 2011/0015941 A1 | 1/2011 | Backhaus |
| 2011/0046975 A1 | 2/2011 | Hoffman |
| 2011/0060758 A1 | 3/2011 | Schlotterbeck et al. |
| 2011/0078608 A1 | 3/2011 | Gannon et al. |
| 2011/0119612 A1 | 5/2011 | Gannon et al. |
| 2011/0179405 A1 | 7/2011 | Dicks et al. |
| 2011/0202495 A1 | 8/2011 | Gawlick |
| 2011/0282691 A1 | 11/2011 | Coffman et al. |
| 2011/0288882 A1 | 11/2011 | Halow |
| 2011/0313787 A1 | 12/2011 | Rangadass et al. |
| 2012/0011253 A1 | 1/2012 | Friedman et al. |
| 2012/0016215 A1 | 1/2012 | Condurso et al. |
| 2012/0041775 A1 | 2/2012 | Cosentino et al. |
| 2012/0053533 A1 | 3/2012 | Butterfield et al. |
| 2012/0075060 A1 | 3/2012 | Connor |
| 2012/0075061 A1 | 3/2012 | Barnes |
| 2012/0136673 A1 | 5/2012 | Presley et al. |
| 2012/0173264 A1 | 7/2012 | Brush et al. |
| 2012/0173391 A1 | 7/2012 | Korhnak et al. |
| 2012/0179006 A1 | 7/2012 | Jansen et al. |
| 2012/0182939 A1 | 7/2012 | Rajan et al. |
| 2012/0185267 A1 | 7/2012 | Kamen et al. |
| 2012/0191052 A1 | 7/2012 | Rao |
| 2012/0239824 A1 | 9/2012 | Nguyen et al. |
| 2012/0241043 A1 | 9/2012 | Perazzo |
| 2012/0247480 A1 | 10/2012 | Varga |
| 2012/0253835 A1 | 10/2012 | Tracy et al. |
| 2012/0265549 A1 | 10/2012 | Virolainen |
| 2013/0018356 A1 | 1/2013 | Prince et al. |
| 2013/0085771 A1 | 4/2013 | Ghanbari et al. |
| 2013/0096444 A1 | 4/2013 | Condurso et al. |
| 2013/0197927 A1 | 8/2013 | Vanderveen et al. |
| 2013/0197928 A1 | 8/2013 | Vanderveen et al. |
| 2013/0197929 A1 | 8/2013 | Vanderveen et al. |
| 2013/0197930 A1 | 8/2013 | Garibaldi et al. |
| 2013/0197931 A1 | 8/2013 | Gupta et al. |
| 2013/0204433 A1 | 8/2013 | Gupta et al. |
| 2013/0204637 A1 | 8/2013 | Vanderveen et al. |
| 2013/0262138 A1 | 10/2013 | Jaskela et al. |
| 2014/0028464 A1 | 1/2014 | Garibaldi |
| 2014/0100868 A1 | 4/2014 | Condurso et al. |
| 2014/0278466 A1 | 9/2014 | Simmons et al. |
| 2014/0297313 A1 | 10/2014 | Condurso et al. |
| 2014/0350950 A1 | 11/2014 | Jaskela et al. |
| 2015/0250948 A1 | 9/2015 | Gupta et al. |
| 2016/0000997 A1 | 1/2016 | Batch et al. |
| 2016/0114925 A1 | 4/2016 | Yuyama |

FOREIGN PATENT DOCUMENTS

| | | | |
|---|---|---|---|
| CN | 1421810 | A | 6/2003 |
| CN | 1650317 | A | 8/2005 |
| CN | 1759398 | | 4/2006 |
| CN | 1803103 | | 7/2006 |
| CN | 101116077 | | 1/2008 |
| CN | 101146055 | | 3/2008 |
| CN | 201110955 | | 9/2008 |
| CN | 101331491 | | 12/2008 |
| CN | 101689320 | | 3/2010 |
| CN | 101890193 | | 11/2010 |
| CN | 102068725 | | 5/2011 |
| CN | 102508877 | | 6/2012 |
| CN | 102521394 | | 6/2012 |
| CN | 102688532 | | 9/2012 |
| CN | 102799783 | | 11/2012 |
| DE | 4023785 | | 1/1992 |
| EP | 0192786 | | 9/1986 |
| EP | 0384155 | | 8/1990 |
| EP | 0595474 | | 5/1994 |
| EP | 0649316 | | 4/1995 |
| EP | 0652528 | | 5/1995 |
| EP | 0784283 | | 7/1997 |
| EP | 0921488 | | 6/1999 |
| EP | 1003121 | | 5/2000 |
| EP | 1018347 | | 7/2000 |
| EP | 1237113 | | 9/2002 |
| EP | 1750573 | A1 | 2/2007 |
| GB | 2141006 | | 12/1984 |
| JP | 62114562 | | 5/1987 |
| JP | 5168708 | | 7/1993 |
| JP | 11505352 | | 5/1999 |
| JP | 2002520718 | | 7/2002 |
| JP | 2003085283 | | 3/2003 |
| JP | 2004287616 | | 10/2004 |
| JP | 2005165442 | A | 6/2005 |
| JP | 2005296428 | A | 10/2005 |
| JP | 2006155070 | | 6/2006 |
| JP | 2006521183 | A | 9/2006 |
| JP | 2008508616 | | 3/2008 |
| JP | 2008516303 | A | 5/2008 |
| JP | 2011501311 | A | 1/2011 |
| JP | 2012200430 | A | 10/2012 |
| KR | 1020070045611 | | 5/2007 |
| KR | 1020080013129 | | 2/2008 |
| KR | 100847397 | | 7/2008 |
| KR | 1020100125972 | | 12/2010 |
| KR | 1020110070824 | | 6/2011 |
| KR | 1020120076615 | | 7/2012 |
| KR | 1020120076635 | | 7/2012 |
| NZ | 522631 | | 7/2004 |
| WO | WO-1993022735 | | 11/1993 |
| WO | WO-1994005344 | | 3/1994 |
| WO | WO-1994008647 | | 4/1994 |
| WO | WO-1994013250 | | 6/1994 |
| WO | WO-1995023378 | | 8/1995 |
| WO | WO-1996020745 | | 7/1996 |
| WO | WO-1996025214 | | 8/1996 |
| WO | WO-1996036923 | | 11/1996 |
| WO | WO-1997004712 | | 2/1997 |
| WO | WO-1998013783 | | 4/1998 |
| WO | WO-1998028676 | | 7/1998 |
| WO | WO-1999009505 | | 2/1999 |
| WO | WO-1999010829 | | 3/1999 |
| WO | WO-1999010830 | | 3/1999 |

(56) References Cited

FOREIGN PATENT DOCUMENTS

| | | |
|---|---|---|
| WO | WO1999035588 | 7/1999 |
| WO | WO-1999044167 | 9/1999 |
| WO | WO-1999045490 | 9/1999 |
| WO | WO-1999046718 | 9/1999 |
| WO | WO-1999067732 | 12/1999 |
| WO | WO-2000003344 | 1/2000 |
| WO | WO-2000004521 | 1/2000 |
| WO | WO-2000018449 | 4/2000 |
| WO | WO-2000032088 | 6/2000 |
| WO | WO-2000032098 | 6/2000 |
| WO | WO-2001086506 | 11/2001 |
| WO | WO-2001088828 | 11/2001 |
| WO | WO-2002036044 | 5/2002 |
| WO | WO-2002069099 | 9/2002 |
| WO | WO-2003038566 | 5/2003 |
| WO | WO-2003053503 | 7/2003 |
| WO | WO-2003092769 | 11/2003 |
| WO | WO-2003094091 | 11/2003 |
| WO | WO-2004060443 | 7/2004 |
| WO | WO-2004061745 | 7/2004 |
| WO | WO-2002053209 A1 | 10/2004 |
| WO | WO-2005110208 A1 | 11/2005 |
| WO | WO-2008087982 A1 | 5/2010 |
| WO | WO-2010124016 | 10/2010 |
| WO | WO-2010124328 | 11/2010 |
| WO | WO-2012095829 | 7/2012 |
| WO | WO-2014159280 | 10/2014 |

OTHER PUBLICATIONS

Canadian Office Action for Application No. 2901024, dated Jul. 20, 2022, 5 pages.
Chinese Office Action for Application No. 202111564727.9, dated Aug. 17, 2022, 14 pages including translation.
Brazilian Office Action for Application No. BR112015029135-0, dated Mar. 8, 2022, 8 pages including translation.
Chinese Office Action for Application No. 201480015093.3, dated Mar. 3, 2022, 42 pages including translation.
"General-Purpose Infusion Pumps," Evaluation—Health Devices, Oct. 2002, pp. 353-387, vol. 31 (10), ECRI Institute.
"Infusion Pump Technology," Health Devices, Apr.-May 1998, pp. 150-170, vol. 27(4-5), ECRI Institute.
"Infusion Pumps, General Purpose," Healthcare Product Comparison System, 2007, pp. 1-54, ECRI Institute.
"Infusion Pumps, Large-Volume," Healthcare Product Comparison System, 2010, pp. 1-51, ECRI Institute.
"Smart Infusion Pumps Join CPOE and Bar Coding as Important Ways to Prevent Medication Errors," ISMP—Medication Safety Alert, Feb. 7, 2002, 2 pgs., Institute for Safe Medication Practices.
Anonymous, Guardrails® Safety Software—Medley TM Medication Safety System, Alaris Medical Systems XP-00234431; 2002 Alaris Medical Systems Inc. Nov. 2002, SSM @2159C.
Australia Office Action for Application No. 2014268828, dated Jul. 3, 2020, 5 pages.
Australian Decision Issued for Application No. 2014268828, dated Feb. 26, 2021, 30 pages.
Australian Examination Report No. 1 for Application No. 2016216550, dated Sep. 20, 2017, 3 pages.
Australian Examination Report No. 2 for Application No. 2012228997, dated Dec. 11, 2015, 3 pages.
Australian Office Action for Application No. 2006213718, dated Jul. 8, 2010, 4 pages.
Australian Office Action for Application No. 2006213718, dated Sep. 19, 2011, 3 pages.
Australian Office Action for Application No. 2014241019, dated Aug. 12, 2019, 4 pages.
Australian Office Action for Application No. 2014241019, dated Dec. 5, 2019, 5 pages.
Australian Office Action for Application No. 2014241019, dated Feb. 6, 2019, 3 pages.
Australian Office Action for Application No. 2014241022, dated Feb. 7, 2019, 4 pages.
Australian Office Action for Application No. 2014241022, dated Jun. 25, 2019, 3 pages.
Australian Office Action for Application No. 2014241022, dated Sep. 30, 2019, 4 pages.
Australian Office Action for Application No. 2014268828, dated Jul. 26, 2019, 4 pages.
Australian Office Action for Application No. 2014268828, dated Nov. 25, 2019, 3 pages.
Australian Office Action for Application No. 2018232958, dated Aug. 7, 2019, 3 pages.
Australian Office Action for Application No. 2020200812, dated Mar. 24, 2021, 5 pages.
Australian Office Action for Application No. 2020201641, dated Oct. 9, 2020, 4 pages.
Australian Office Action for Application No. 2020203449, dated May 26, 2021, 5 pages.
Baldauf-Sobez et al., "How Siemens' Computerized Physician Order Entry Helps Prevent the Human Errors," electromedica, vol. 71, No. 1, 2003, pp. 2-10.
Brazil Office Action for Application No. BR112015019758-2, dated Feb. 20, 2020, 5 pages.
Brazil Office Action for Application No. BR112015029135-0, dated Feb. 12, 2020, 5 pages.
Calabrese, et al., "Medication administration errors in adult patients in the ICU," Intensive Care Med, 2001, pp. 1592-1598, vol. 27, Springer-Verlag.
Canada Office Action for Application No. 2900564, dated Jan. 28, 2020, 4 pages.
Canadian Office Action for Application No. 2512991, dated Jan. 10, 2018, 4 pages.
Canadian Office Action for Application No. 2512991, dated Mar. 2, 2017, 4 pages.
Canadian Office Action for Application No. 2551903, dated Aug. 18, 2020, 3 pages.
Canadian Office Action for Application No. 2551903, dated Mar. 28, 2017, 7 pages.
Canadian Office Action for Application No. 2551903, dated Mar. 5, 2018, 8 pages.
Canadian Office Action for Application No. 2596881, dated Dec. 20, 2012, 1 page.
Canadian Office Action for Application No. 2828898, dated Aug. 25, 2021, 5 pages.
Canadian Office Action for Application No. 2828898, dated Dec. 3, 2019, 6 pages.
Canadian Office Action for Application No. 2828898, dated Dec. 7, 2018, 5 pages.
Canadian Office Action for Application No. 2828898, dated Jan. 11, 2018, 8 pages.
Canadian Office Action for Application No. 2828898, dated Oct. 7, 2020, 7 pages.
Canadian Office Action for Application No. 2900564, dated Nov. 19, 2020, 4 pages.
Canadian Office Action for Application No. 2901024, dated Aug. 25, 2021, 6 pages.
Canadian Office Action for Application No. 2901024, dated Jan. 27, 2020, 5 pages.
Canadian Office Action for Application No. 2901024, dated Nov. 20, 2020, 6 pages.
Canadian Office Action for Application No. 2912792, dated Mar. 1, 2021, 7 pages.
Chinese First Office Action for Application No. 2012800136388, dated Jul. 23, 2015, 15 pages.
Chinese Notice of Reexamination for Application No. 201480015025.7, dated Aug. 20, 2021, 29 pages including translation.
Chinese Notice of Reexamination for Application No. 201480015036.5, dated Jul. 29, 2021, 32 pages including machine translation.
Chinese Office Action for Application No. 2 1480041362.3, dated Oct. 18, 2018, 13 pages.
Chinese Office Action for Application No. 2012800136388, dated Jul. 18, 2016, 2 pages excluding machine translation.

(56) References Cited

OTHER PUBLICATIONS

Chinese Office Action for Application No. 201480015025.7, dated Jan. 23, 2018, 11 pages excluding English summary.
Chinese Office Action for Application No. 201480015025.7, dated Jun. 24, 2019, 25 pages.
Chinese Office Action for Application No. 201480015025.7, dated Nov. 12, 2019, 20 pages.
Chinese Office Action for Application No. 201480015025.7, dated Oct. 9, 2018, 27 pages.
Chinese Office Action for Application No. 201480015036.5, dated Jan. 23, 2018, 13 pages excluding English translation.
Chinese Office Action for Application No. 201480015036.5, dated Jun. 24, 2019, 20 pages.
Chinese Office Action for Application No. 201480015036.5, dated Nov. 5, 2019, 12 pages.
Chinese Office Action for Application No. 201480015036.5, dated Sep. 29, 2018, 20 pages.
Chinese Office Action for Application No. 201480015093.3, dated Apr. 25, 2019, 18 pages.
Chinese Office Action for Application No. 201480015093.3, dated Dec. 4, 2019, 17 pages.
Chinese Office Action for Application No. 201480015093.3, dated Jul. 16, 2018, 16 pages.
Chinese Office Action for Application No. 201480015147.6, dated Mar. 10, 2017, 10 pages excluding translation.
Chinese Office Action for Application No. 201480015147.6, dated May 3, 2018, 6 pages.
Chinese Office Action for Application No. 201480015147.6, dated Nov. 16, 2017, 8 pages.
Chinese Office Action for Application No. 201480041985.0, dated Apr. 3, 2019, 12 pages.
Chinese Office Action for Application No. 201480041985.0, dated Jun. 2, 2021, 4 pages including translation.
Chinese Office Action for Application No. 201480041985.0, dated May 15, 2020, 23 pages.
Chinese Office Action for Application No. 201480041985.0, dated Sep. 23, 2019, 24 pages.
Chinese Office Action for Application No. 201480041985.0, dated Sep. 3, 2020, 38 pages.
Chinese Second Office Action for Application No. 201280013638.8, dated Feb. 15, 2016, 8 pages excluding translation.
Eskew, James et al., Using Innovative Technologies To Set New Safety Standards For The Infusion Of Intravenous Medications, Hospital Pharmacy, vol. 37, No. 11, pp. 1179-1189, 2002, Facts and Comparisons.
European Communication for Application No. 14779655.1, dated Oct. 2, 2019, 12 pages.
European Communication of the Board of Appeal for Application No. 05791269.3, dated Nov. 10, 2017, 7 pages.
European Office Action for Application No. 06720651.6, dated May 5, 2008, 3 pages.
European Office Action for Application No. 12756903.6, dated Apr. 19, 2017, 5 pages.
European Office Action for Application No. 14772937.0, dated Apr. 19, 2018, 9 pages.
European Office Action for Application No. 14775918.7, dated Dec. 20, 2017, 8 pages.
European Office Action for Application No. 14779655.1, dated Jul. 28, 2017, 6 pages.
European Office Action for Application No. 14779655.1, dated Mar. 8, 2018, 7 pages.
European Office Action for Application No. 14801713.0, dated Dec. 11, 2019, 6 pages.
European Office Action for Application No. 20191537.8, dated Aug. 18, 2021, 10 pages.
European Summons to attend oral proceedings pursuant to Rule 115(1) EPC for Application No. 14772937.0, dated Jul. 17, 2019, 12 pages.
Evans, R. S. et al., "Enhanced notification of infusion pump programming errors", Studies in health technology and informatics, Jan. 1, 2010, pp. 734-738, XP055305644, Netherlands DOI: 10.3233/978-1-60750-588-4-734 Retrieved from the Internet: URL:http://booksonline.iospress.nl/Extern/EnterMedLine.aspx?ISSN=0926-9630&Volume=160&SPage=734 [retrieved on Sep. 26, 2016].
Extended European Search Report and Written Opinion for Application No. 14772937.0, dated Oct. 10, 2016, 9 pages.
Extended European Search Report and Written Opinion for Application No. 14775918.7, dated Sep. 13, 2016, 10 pages.
Extended European Search Report and Written Opinion for Application No. 14779139.6, dated Nov. 7, 2016, 7 pages.
Extended European Search Report for Application No. 14779655.1, dated Jul. 14, 2016, 8 pages.
Extended European Search Report for Application No. 14780320.9, dated Jul. 1, 2016, 7 pages.
Extended European Search Report for Application No. 14801713.0, dated Jan. 16, 2017, 8 pages.
Extended European Search Report for Application No. 14801726.2, dated Jan. 5, 2017, 8 pages.
Extended European Search Report for Application No. 20191537.8, dated Dec. 17, 2020, 9 pages.
Hickle, WO 2004/060443, Appartuses and Method for Automatically Assessing and Monitoring a Patient's Responsiveness, Dec. 23, 2003.
India Office Action for Application No. 2625/KOLNP/2015, dated Jul. 8, 2020, 7 pages.
India Office Action for Application No. 4041/KOLNP/2015, dated Jul. 8, 2020, 8 pages.
India Office Action for Application No. 7050/CHENP/2013, dated Sep. 18, 2019, 7 pages.
International Preliminary Report on Patentability for Application No. PCT/US2004/000443, dated Nov. 30, 2004, 3 pages.
International Search Report and Written Opinion for Application No. PCT/US2004/043531, dated Sep. 22, 2005, 12 pages.
International Search Report and Written Opinion for Application No. PCT/US2005/029993, dated Jan. 23, 2006, 17 pages.
International Search Report and Written Opinion for Application No. PCT/US2013/029993, dated Feb. 4, 2014, 9 pages.
International Search Report and Written Opinion for Application No. PCT/US2014/023681, dated Jul. 14, 2014, 12 pages.
International Search Report and Written Opinion for PCT Application No. PCT/US2014/022830, dated Jun. 19, 2014, 6 pages.
International Search Report and Written Opinion for PCT Application No. PCT/US2014/022832, dated Jun. 24, 2014, 5 pages.
International Search Report and Written Opinion for PCT Application No. PCT/US2014/022835.
International Search Report and Written Opinion for PCT Application No. PCT/US2014/022837, dated Jun. 18, 2014.
International Search Report and Written Opinion for PCT Application No. PCT/US2014/022840, dated Jun. 19, 2014, 5 pages.
International Search Report and Written Opinion for PCT Application No. PCT/US2014/037577 dated Sep. 5, 2014.
International Search Report and Written Opinion for PCT/US2012/029544 dated Sep. 28, 2012, 8 pages.
International Search Report and Written Opinion in PCT Application No. PCT/US2014/039228 dated Aug. 22, 2014, 11 pgs.
International Search Report for Application No. PCT/US2001/15989, dated Nov. 28, 2002, 3 pages.
International Search Report for Application No. PCT/US2014/023685, dated Jul. 9, 2014, 4 pages.
International Search Report for Application No. PCT/US2014/038497, dated Oct. 23, 2014, 3 pages.
International Search Report for PCT Application No. PCT/US2004/000443 dated Sep. 1, 2004.
International Search Report for PCT Application No. PCT/US2006/004864.
Japanese Office Action for Application No. 2016-501081, dated May 7, 2019, 4 pages.
Japanese Office Action for Application No. 2016501081, dated Nov. 12, 2019, 6 pages.
Japanese Office Action for Application No. 2016-501081, dated Nov. 2, 2018, 6 pages.
Japanese Office Action for Application No. 2019-030891, dated Aug. 24, 2021, 4 pages including translation.

(56) References Cited

OTHER PUBLICATIONS

Japanese Office Action for Application No. 2019-030891, dated May 27, 2020, 8 pages.
Japanese Office Action for Application No. 2019-030891, dated Nov. 26, 2020, 5 pages including English translation.
Japanese Office Action in Application No. 2016-501081, dated Feb. 9, 2018, 4 pages.
Japanese Office Action in JP Application No. 2004-565078 dated Aug. 3, 2009.
Kohn, et al., "To Err is Human—Building a Safer Health System," National Academy Press, 2002, pp. i-i287, National Academy of Sciences.
Lesar, "Recommendations for Reducing Medication Errors," Medscape Pharmacists, posted Jul. 24, 2000, 10 pgs, vol. 1(2), Medscape Pharmacists, <http://www.medscape.com>.
Meier, "Hospital Products Get Seal of Approval at a Price," The New York Times, Apr. 23, 2002, 5 pgs.
Memo concerning Mexican Office Action for Application No. MX/a/2015/015959, dated Sep. 21, 2017, 4 pages.
Memo concerning Mexican Office Action for Application No. MX/a/2015/015959, dated Mar. 2, 2018, 1 page.
New Zealand Examination Report for Application No. 560278, dated Jun. 23, 2009, 1 page.
Non-Final Office Action dated Oct. 14, 2014, issued in U.S. Appl. No. 11/326,145.
Non-Final Office Action dated Oct. 14, 2014, issued in U.S. Appl. No. 13/559,537.
Office Action dated Aug. 19, 2013; issued in U.S. Appl. No. 13/246,782.
Office Action for U.S. Appl. No. 09/860,865 dated Jul. 25, 2014.
Office Action for U.S. Appl. No. 13/802,433.
Office Action for U.S. Appl. No. 13/802,683.
Office Action for UAE Application No. UAE/P/353/2002 dated Jan. 25, 2011.
Office Action for United Arab Emirates Application No. UAE/P/0962/2013, dated Apr. 17, 2017, 18 pages.
Office Action issued in U.S. Appl. No. 13/802,446 dated Aug. 13, 2014.
Queensland Health. Use of returned or unused dispensed medicines, Jan. 5, 2005, Queensland Government. pp. 1-2.
Shabot et al., "Wireless clinical alerts for critical medication, laboratory and physiologic data," System Sciences 2000. Proceedings of the 33rd Annual Conference on Jan. 4-7, 2000, Piscataway, NJ, IEEE, Jan. 4, 2000.
Translation of Japanese Office Action in JP Application No. 2006547436 dated Apr. 1, 2011.
U.S. Appl. No. 90/009,912, filed Aug. 12, 2013, Schlotterbeck et al.
U.S. Appl. No. 90/011,697, filed Aug. 12, 2013, Schlotterbeck et al.
United Arab Emirates Office Action from KIPO for Application No. UAE/P/1554/2015, first received Nov. 21, 2019, 11 pages.
U.S. Office Action in U.S. Appl. No. 13/421,776 dated Oct. 9, 2013, 35 pages.
U.S. Appl. No. 13/901,501, filed May 23, 2013.
Williams, et al., "Reducing the Risk of User Error with Infusion Pumps," Professional Nurse—Safe Practice—Infusion Devices, Mar. 2000, pp. 382-384, vol. 15(6).
Written Opinion for Application No. PCT/US2004/000443, dated Jun. 22, 2005, 5 pages.
Written Opinion for Application No. PCT/US2006/004864, dated Jun. 22, 2006, 5 pages.
Yokoi, "Prevention of Errors in Injection/Drip Infusion—No excuse for ignorance!—Essential Points of Accident Prevention, IV Infusion Pump, Syringe-pump Accident Prevention," JIN Special, Igaku Shoin K.K., Dec. 1, 2001, pp. 109-120, No. 70.
Australian Office Action for Application No. 2020200812, dated Nov. 18, 2021, 4 pages.
Canadian Office Action for Application No. 2912792, dated Dec. 30, 2021, 9 pages.
Australian Office Action for Application No. 2020203449, dated Nov. 24, 2021, 3 pages.
Australian Office Action for Application No. 2020210162, dated Sep. 22, 2021, 6 pages.
Chinese Office Action for Application No. 201480015036.5, dated Sep. 24, 2021, 52 pages including translation.
Chinese Office Action for Application No. 201480015093.3, dated Nov. 1, 2021, 36 pages including translation.
Australian Office Action for Application No. 2022201089, dated Mar. 17, 2023, 3 pages.
Chinese Office Action for Application No. 202111564727.9, dated Mar. 19, 2023, 14 pages including translation.
Extended European Search Report for Application No. 22205566.7, dated Mar. 13, 2023, 12 pages.
India Hearing Notice for Application No. 4041/KOLNP/2015, dated Apr. 6, 2023, 5 pages.
Chinese Office Action for Application No. 202111564727.9, dated Aug. 2, 2023, 12 pages including translation.

\* cited by examiner

FIG. 9

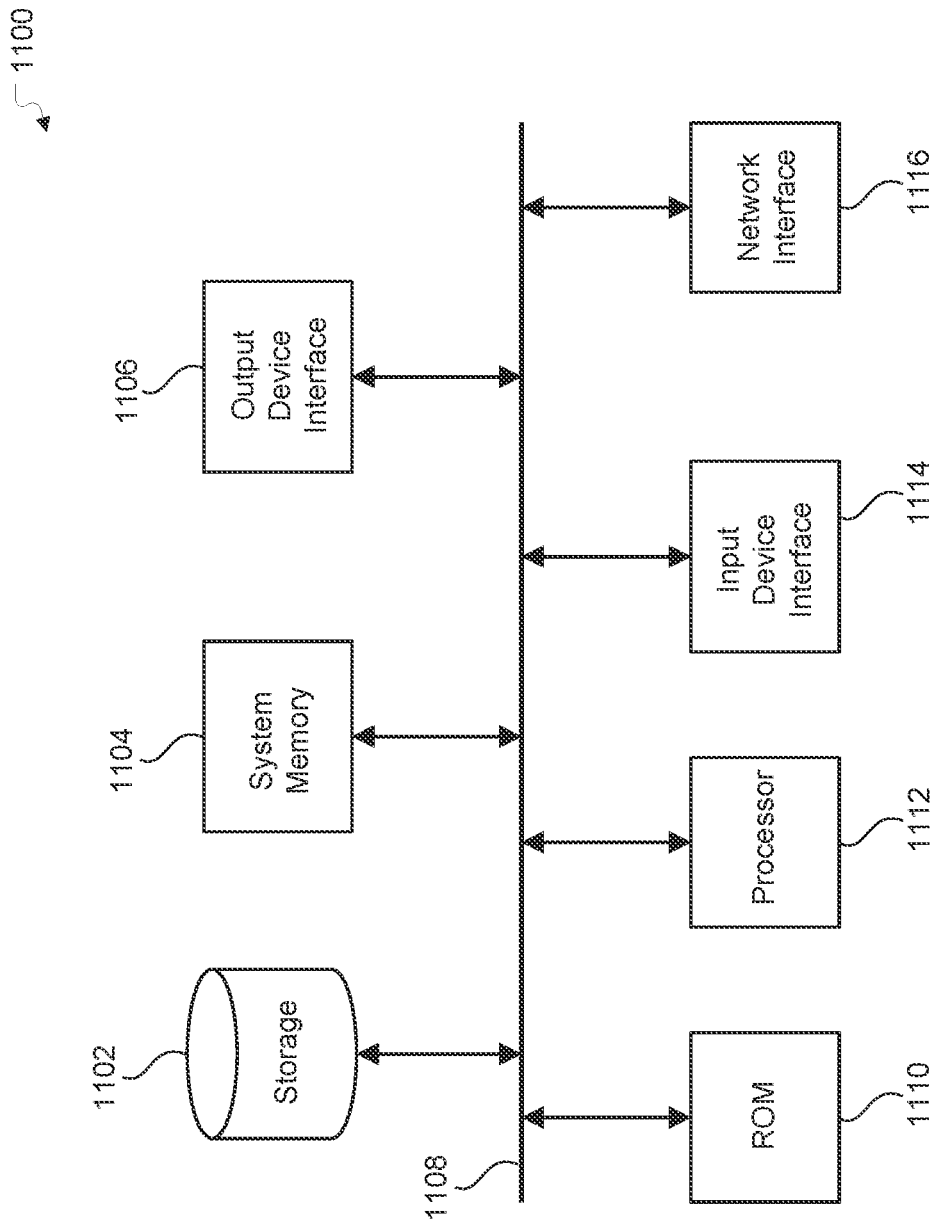

CONTEXT-AWARE HEALTHCARE NOTIFICATION SYSTEM

CROSS-REFERENCE TO RELATED APPLICATIONS

The present application is a continuation of U.S. patent application Ser. No. 13/802,446, entitled "Context-Aware Healthcare Notification System," filed on Mar. 13, 2013, now U.S. Pat. No. 11,087,873, which is a continuation-in-part of U.S. patent application Ser. No. 09/860,865, entitled "Distributed Remote Asset and Medication Management Drug Delivery System," filed on May 18, 2001, now issued as U.S. Pat. No. 9,600,633, which claims priority to U.S. Provisional Patent Application Ser. No. 60/205,125, entitled "Distributed remote asset and medication management drug delivery system (DRAMMDDS)," filed on May 18, 2000, both of which are hereby incorporated by reference in their entirety for all purposes. U.S. patent application Ser. No. 13/802,446 is also a continuation-in-part of U.S. patent application Ser. No. 10/361,704, entitled "Medication Management and Event Logger and Analysis System," filed on Feb. 9, 2003, which is hereby incorporated by reference in its entirety for all purposes. U.S. patent application Ser. No. 13/802,446 is also a continuation-in-part of U.S. patent application Ser. No. 10/750,032, entitled "Centralized Medication Management System," filed on Dec. 31, 2003, which is hereby incorporated by reference in its entirety for all purposes. U.S. patent application Ser. No. 13/802,446 is also a continuation-in-part of U.S. patent application Ser. No. 13/246,782, entitled "System and Method for Dynamically Adjusting Patient Therapy," filed on Sep. 27, 2011, which is a continuation of U.S. patent application Ser. No. 12/947,773, entitled "System and Method for Dynamically Adjusting Patient Therapy," filed on Nov. 16, 2010, now issued as U.S. Pat. No. 8,340,792, which is a continuation of U.S. patent application Ser. No. 10/925,511, entitled "System and Method for Dynamically Adjusting Patient Therapy," filed on Aug. 25, 2004, now issued as U.S. Pat. No. 7,860,583, all of which are hereby incorporated by reference in their entirety for all purposes. U.S. patent application Ser. No. 13/802,446 is also a continuation-in-part of U.S. patent application Ser. No. 11/326,145, entitled "Management of Pending Medication Orders," filed on Dec. 30, 2005, now issued as U.S. Pat. No. 9,427,520, which claims priority to U.S. Provisional Patent Application Ser. No. 60/652,382, entitled "Management of Pending Medication Orders," filed on Feb. 11, 2005, both of which are hereby incorporated by reference in their entirety for all purposes.

TECHNICAL FIELD

The present description relates generally to a notification system, and more particularly, but not exclusively, to a context-aware healthcare notification system.

BACKGROUND

Healthcare facilities, such as hospitals, may utilize many different user devices, healthcare devices, and/or healthcare systems to facilitate with providing healthcare to patients. For example, a healthcare facility may utilize healthcare systems to facilitate with providing healthcare to patients, such as through physician order entry systems, pharmacy information systems, hospital information systems, etc. The healthcare facility may also utilize healthcare devices to facilitate with providing healthcare to patients, such as infusion devices, dispensing devices, respiratory devices, etc. In addition, the healthcare facility may utilize user devices to facilitate with providing healthcare to patients, such as computing stations that are located throughout the health facility, personal digital assistants (PDAs) that are carried by health care professionals, etc. However, the healthcare facility may be unable to provide relevant information from the healthcare systems and healthcare devices to the user devices in a timely manner.

SUMMARY

The disclosed subject matter relates to a user device for facilitating healthcare. The user device may include a processor and a memory. The memory may include instructions that, when executed by the processor, cause the processor to: determine when the user device is within proximity of at least one healthcare device, receive information pertaining to the at least one healthcare device when the device is within the proximity of the at least one healthcare device, and display at least a portion of the received information.

The disclosed subject matter also relates to a user device for facilitating healthcare that includes a wireless interface, a receiver, a processor, and a display. The wireless interface may be configured to determine when the user device is located within a proximity of a patient. The receiver may be configured to receive information related to the patient when the user device is located within the proximity of the patient. The processor may be configured to determine whether the information indicates that corrective action is required. The display may be configured to display at least a portion of the information when the information indicates that corrective action is required.

The disclosed subject matter also relates to a method for providing for providing context sensitive information to a user device. The method includes determining, by a user device, that the user device is within a proximity of a patient or a healthcare device. The method further includes receiving, by the device, information that relates to the patient or the healthcare device and determining, by the device, whether the information indicates that corrective action is required or a safety issue exists. The method further includes displaying, by the device, at least a portion of the information when the information indicates that the corrective action is required or the safety issue exists.

The disclosed subject matter also relates to a system. The system includes one or more processors and a memory. The memory includes instructions that, when executed by the one or more processors, cause the one or more processors to: determine when a user device is within a proximity of at least one healthcare device or at least one patient, receive first information related to the at least one healthcare device or the at least one patient from a plurality of healthcare systems over a communication network, when the user device is determined to be within the proximity of the at least one healthcare device or the at least one patient, and transmit, to the user device over the communication network, at least a portion of the first information related to the at least one healthcare device or the at least one patient.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

Certain features of the subject technology are set forth in the appended claims. However, for purpose of explanation, several embodiments of the subject technology are set forth in the following figures.

FIG. 9 illustrates an example user interface that may be implemented in a context-aware healthcare notification system in accordance with one or more embodiments.

FIG. 11 conceptually illustrates an electronic system with which one or more embodiments of the subject technology may be implemented.

DETAILED DESCRIPTION

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be clear and apparent to those skilled in the art that the subject technology is not limited to the specific details set forth herein and may be practiced using one or more embodiments. In one or more instances, well-known structures and components are shown in block diagram form in order to avoid obscuring the concepts of the subject technology.

Figure 1:
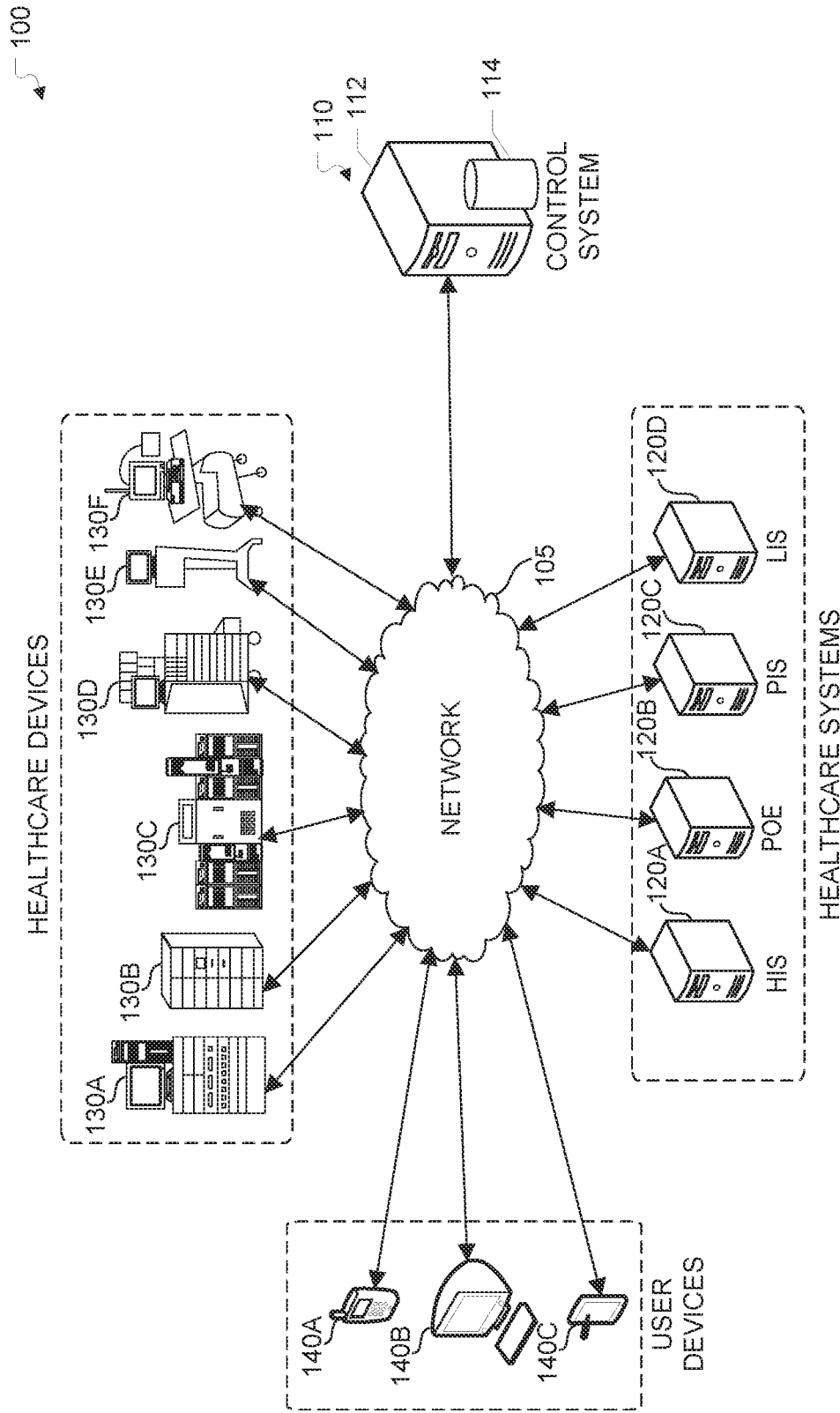
FIG. 1 illustrates an example network environment in which a context-aware healthcare notification system may be implemented in accordance with one or more embodiments.

FIG. 1 illustrates an example network environment 100 in which a context-aware healthcare notification system may be implemented in accordance with one or more embodiments. Not all of the depicted components may be required, however, and one or more embodiments may include additional components not shown in the figure. Variations in the arrangement and type of the components may be made without departing from the spirit or scope of the claims as set forth herein. Additional, different or fewer components may be provided.

The network environment 100 includes network 105, a control system 110, one or more healthcare systems 120A-D, one or more healthcare devices 130A-F, and one or more user devices 140A-C. The control system 110, healthcare systems 120A-D, healthcare devices 130A-F, and/or user devices 140A-C may be communicatively coupled to one another, such as by the network 105. In one or more embodiments, one or more of the control system 110, healthcare systems 120A-D, healthcare devices 130A-F, or user devices 140A-C may be directly coupled to one another. In addition, there may be a number of other devices connected to the network 105, such as additional healthcare systems, e.g. other clinical and/or logistical systems, additional healthcare devices, external systems, computing devices, mobile devices, etc. The control system 110, one or more healthcare systems 120A-D, one or more healthcare devices 130A-F, and/or one or more user devices 140A-C may be, or may include all or part of, the electronic system that is discussed further below with respect to FIG. 11.

The network 105 may be a communication network, such as a public communication network (such as the Internet, cellular data network, dialup modems over a telephone network), a private communications network (such as private local area network ("LAN"), leased lines), etc. The network 105 may also include, but is not limited to, any one or more of the following network topologies, including a bus network, a star network, a ring network, a mesh network, a star-bus network, a tree or hierarchical network, and the like. The connections of the network 105 may be wired or wireless. For example, one or more of the control system 110, healthcare systems 120A-D, healthcare devices 130A-F, and/or user devices 140A-C may transmit wireless signals over the network 105, such as radio frequency (RF) signals, infrared (IR) signals, Bluetooth signals, or any other means capable of carrying information in a wireless manner between devices having appropriate transmitters and/or receivers.

The control system 110 may be a single computing device such as a computer server. Alternatively, the control system 110 may represent one or more computing devices (such as a cloud of computers and/or a distributed system) that are communicatively coupled, such as communicatively coupled over the network 105, and that collectively, or individually, perform one or more functions that can be performed server-side, such as receiving messages, transmitting messages, storing messaging, receiving control commands, providing user interfaces, transmitting notifications, etc. The one or more computing devices of the control system 110 may be geographically collocated and/or the one or more computing devices of the control system 110 may be disparately located. The control system 110 may be coupled with various databases, such as data store 114, storage services, or other computing devices. The control system 110, and the coupled databases, storage services, or other computing devices may be geographically collocated, or may be disparately located. In one or more embodiments, the control system 110 includes a processing device 112 and a data store 114. The processing device 112 executes computer instructions stored in the data store 114. In one or more embodiments, the data store 114 may store the computer instructions on non-transitory computer-readable medium.

The one or more healthcare systems 120A-D may be any systems that facilitate with providing healthcare, and/or provide healthcare. In FIG. 1, the healthcare system 120A is a hospital information system (HIS), the healthcare system 120B is a physician order entry (POE) system, the healthcare system 120C is a pharmacy information system (PIS), and the healthcare system 120D is a laboratory information system (LIS). The HIS may, for example, store information pertaining to the administration of the healthcare facility, such as a hospital. The HIS may provide, and/or may interface with a server that provides, billing and accounting functions. The POE system may be used, for example, by physicians to enter orders for patients, such as orders for medications to be administered to patients, that are then transmitted to the PIS.

The PIS may store, for example, information pertaining to a pharmacy of a healthcare facility, such as outstanding orders, filled orders, patient medical profiles/histories, etc. For example, the PIS may provide a library of drug allergies and adverse drug interactions against which each incoming order, or prescription, is checked as part of the order entering/drug dispensing process to identify possible allergies and adverse drug interactions and help in preventing administration of drugs to a patient where the patient might be injured by the prescribed course of therapy. Additionally, the PIS may check to determine if any therapies are being duplicated, such as where two or more drugs might be used to treat a diagnosed disease, whether they are synergistic or antagonistic, and whether the prescribed therapy should be modified accordingly. The LIS may store laboratory results, such as for tests performed to facilitate with providing healthcare to patients.

The healthcare devices 130A-F may include infusion devices, such as infusion pumps, drug delivery devices, dispensing devices, such as automated dispensing machines, smart beds, monitoring devices, respiratory devices, such as ventilators, waste devices, such as drug disposal devices, or generally any device that may facilitate with providing healthcare and/or may provide healthcare. The healthcare devices 130A-F may include a processor and memory. Alternatively, or in addition, the healthcare devices 130A-F may be communicatively coupled to a device that includes a processor and a memory, such as via a serial port.

For example, the healthcare devices 130A-F may include Pyxis Medstations™ to store and dispense medications at the nurses stations, providing distributed access to the medications needed to treat patients, Pyxis® Anesthesia Systems to store and manage the medications used by anesthesiologists in the operating room, Pyxis SpecialtyStations™ to store specific medications and supplies in individual treatment areas, and Pyxis OncologyStations™ in oncology departments to manage the specialized and hazardous medications used to treat cancer. The healthcare devices 130A-F may also include waste devices that accept and store wasted medications, e.g. excess medications, from healthcare professionals and track the amount of medications wasted by healthcare professionals. In one or more embodiments, one or more of the waste devices may be a Pyxis EcoStation™ system.

The user devices 140A-C may be electronic devices such as laptop or desktop computers, mobile phones, personal digital assistants ("PDAs"), portable media players, tablet computers, televisions or other displays, or other appropriate computing devices that can be used to display user interfaces that facilitate providing healthcare to patients, such as user interfaces that display information related to providing healthcare to patients and/or user interfaces that allow a healthcare professional, such as a doctor or nurse, access, create, and/or modify information related to providing healthcare to patients, such as modifying a schedule for preparing IVs in the PIS. Example user interfaces are discussed further below with respect to FIGS. 7-10. In the example of FIG. 1, the user device 140A is depicted as a mobile phone, the user device 140B is depicted as a desktop computer, and the user device 140C is depicted as a personal digital assistant ("PDA"), e.g. a tablet device. In one or more embodiments, the user devices 140A-C may include a processor and a memory.

In one or more embodiments, the user devices 140A-C may be, may include, and/or may be communicatively coupled to, a Medical Transaction Carrier (MTC). The user devices 140A-C, and/or the MTCs included therein and/or communicatively coupled thereto, may be configured to initiate communication with the control system 110, and/or any of the healthcare devices 130A-F, when the user devices 140A-C are located within a proximity, e.g. a predetermined distance, of any of the healthcare devices 130A-F, and/or within a proximity of one or more patients. Alternatively, or in addition, the control system 110, and/or any of the healthcare devices 130A-F, may be configured to initiate communication with the user devices 140A-C, and/or the MTCs included therein and/or communicatively coupled thereto, when the user devices 140A-C are located within a proximity, e.g. a predetermined distance, of any of the healthcare devices 130A-F, and/or within a proximity of one or more patients.

In one or more embodiments, the user devices 140A-C, and/or the MTCs included therein and/or communicatively coupled thereto, may be configured to initiate communication with any of the healthcare systems 120A-D when the user devices 140A-C are located within a proximity, e.g. a predetermined distance, of any of the healthcare devices 130A-F, and/or within a proximity of one or more patients. Alternatively, or in addition, any of the healthcare systems 120A-D may be configured to initiate communication with the user devices 140A-C, and/or the MTCs included therein and/or communicatively coupled thereto, when the user devices 140A-C are located within a proximity, e.g. a predetermined distance, of any of the healthcare devices 130A-F, and/or within a proximity of one or more patients.

In operation, the control system 110, the healthcare systems 120A-D, the healthcare devices 130A-F, and/or the user devices 140A-C may transmit electronic data streams to one another over the network 105. The messages may relate to healthcare that is being facilitated by any of the healthcare systems 120A-D, the healthcare devices 130A-F, and/or the user devices 140A-C. For example, a message may include an order for a medication that is transmitted from a POE system to a PIS. In one or more embodiments, at least a portion of the message may later be transmitted by the PIS to a healthcare device 130A, such as to indicate that the ordered medication should be administered to the patient. Alternatively, or in addition, a message may relate to the progress of the delivery of medication, such as by one or more of the healthcare devices 130A-F. For example, the healthcare device 130A may transmit a message to the PIS that indicates the progress of delivering the medication by the healthcare device 130A to the patient. For example, the message may indicate that the healthcare device 130A has started delivering the medication, the healthcare device 130A has delivered an indicated amount of the medication, or the healthcare device 130A has completed the delivery of the medication.

The control system 110 may provide user identity and notification systems. For example, the control system 110 may authenticate users and may control the access of a user, or a group of users. For example, a physician may be allowed to input orders into a POE system, while a nurse may only be allowed to view the orders in the POE system. Thus, the control system 110 may provide different views of information, e.g. information received from one or more of the healthcare systems 120A-D and/or the healthcare devices 130A-F, to different users based on the users' access privileges. The control system 110 may also provide user interfaces to users, such as via the user devices 140A-C, and may manage the users' interactions with the user interfaces. In one or more embodiments, the control system 110 may provide information for a patient to a user device 140A to be displayed on one of the user interfaces when the control system 110 determines that the user device 140A is within a proximity of the patient and/or within a proximity of one of the healthcare devices 130A-F that is providing, and/or facilitating with providing, healthcare to the patient. An example process of a context-aware notification system is discussed further below with respect to FIG. 4.

Alternatively, or in addition, the user device 140A may determine that it is located within a proximity of a patient and/or within a proximity of one of the healthcare devices 130A-F. The user device 140A may then transmit an indication to the control system 110 indicating that the user device 140A is located within the proximity of the patient and/or the one of the healthcare devices 130A-F. In response thereto, the control system 110 may transmit information to the user device 140A that pertains to the patient and/or the one of the healthcare devices 130A-F. Example processes for one or more of the user devices 140A-C in a context-aware notification system are discussed further below with respect to FIGS. 5 and 6.

The control system 110 may also transmit notifications to one or more of the users, such as via the user devices 140A-C. For example, the control system 110 may transmit a notification to a user device 140A being accessed by a user, e.g. a user device 140A that the user has authenticated on, when the control system 110 determines that the user is within proximity of a patient who may need care, e.g. a patient that is receiving healthcare from one of the healthcare devices 130A-F that may be experiencing an error. In one or more embodiments, one or more of the notifications may be transmitted to the user devices 140A-C via a user interface. For example, the notification may cause a graphical indicator to be presented on a user interface being displayed on a user device 140A. Example user interfaces for presenting notifications are discussed further below with respect to FIGS. 7 and 10.

Figure 2:
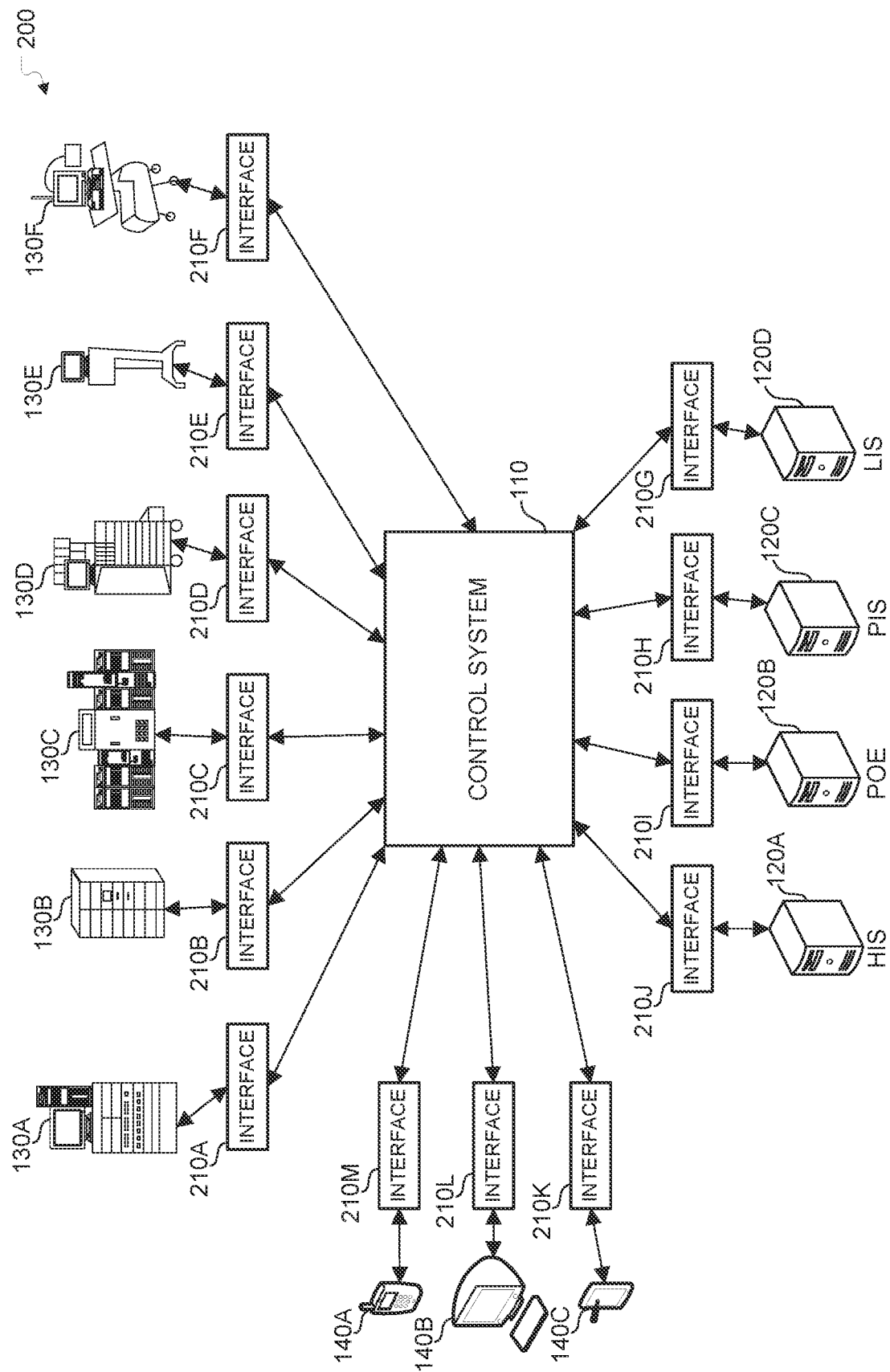
FIG. 2 illustrates an example messaging architecture in which a context-aware healthcare notification system may be implemented in accordance with one or more embodiments.

FIG. 2 illustrates an example messaging architecture 200 in which a context-aware healthcare notification system may be implemented in accordance with one or more embodiments. Not all of the depicted components may be required, however, and one or more embodiments may include additional components not shown in the figure. Variations in the arrangement and type of the components may be made without departing from the spirit or scope of the claims as set forth herein. Additional, different or fewer components may be provided.

The messaging architecture 200 includes the control system 110, one or more healthcare systems 120A-D, one or more healthcare devices 130A-F, and one or more user devices 140A-C. The control system 110, healthcare systems 120A-D, healthcare devices 130A-F, and user devices 140A-C may be communicably coupled to one another, such as by the network 105 shown in FIG. 1. The one or more healthcare systems 120A-D, one or more healthcare devices 130A-F, and one or more user devices 140A-C may include, and/or may be coupled to, interfaces 210A-M. The interfaces 210A-M may be adapters that are utilized by the one or more healthcare systems 120A-D, one or more healthcare devices 130A-F, and one or more user devices 140A-C to transmit messages to one another via the control system 110. In one or more embodiments, the interfaces 210A-M may be, and/or may include, the adapters described in U.S. patent application Ser. No. 13/421,776, entitled "Scalable Communication System," filed on Mar. 15, 2012, which is hereby incorporated by reference in its entirety for all purposes.

In one or more embodiments, messages transmitted by the healthcare systems 120A-D, the healthcare devices 130A-F, and/or the user devices 140A-C may be routed through the control system 110, e.g. via the interfaces 210A-M. For example, if a healthcare device 130A is sending a message to the healthcare system 120C, the healthcare device 130A may utilize the interface 210A to transmit the message to the control system 110, and the control system 110 may forward the message to the interface 210H, which provides the message to the healthcare system 120C. In one or more embodiments, the control system 110 may store the messages, such as in the data store 114, for further processing, such as to identify whether to transmit any information indicated in the messages to one or more of the user devices 140A-C, such as via a notification and/or via a user interface.

In one or more embodiments, the control system 110 may include an interface system that receives the messages from one or more of the healthcare systems 120A-D, the healthcare devices 130A-F, and/or the user devices 140A-C, via the interfaces 210A-M. The interface system may provide the interfaces 210A-M to the one or more of the healthcare systems 120A-D, the healthcare devices 130A-F, and the user devices 140A-C, and the one or more of the healthcare systems 120A-D, the healthcare devices 130A-F, and the user devices 140A-C may transmit messages to the interface system by utilizing the interfaces 210A-M.

In one or more embodiments, the interface system receives the messages in a first external format, e.g. a format native to the transmitting device and/or system, converts the messages into an internal messaging format, e.g. for processing and storing the messages, converts the messages into a second external format, e.g. a format native to the receiving device and/or system, and then transmits the messages in the second external format to the receiving device. In one or more embodiments, the first external format may be the same as the second external format. The interface system may be implemented as described, for example, in U.S. patent application Ser. No. 13/421,776, entitled "Scalable Communication System," filed on Mar. 15, 2012, which has been incorporated by reference in its entirety for all purposes.

Alternatively, or in addition, one or more of the healthcare systems 120A-D, the healthcare devices 130A-F, and/or the user devices 140A-C may communicate with the control system 110 without utilizing the interfaces 210A-M. Alternatively, or in addition, one or more of the healthcare systems 120A-D, the healthcare devices 130A-F, and/or the user devices 140A-C may transmit messages directly to one another, e.g. without routing the messages through the control system 110.

Figure 3:
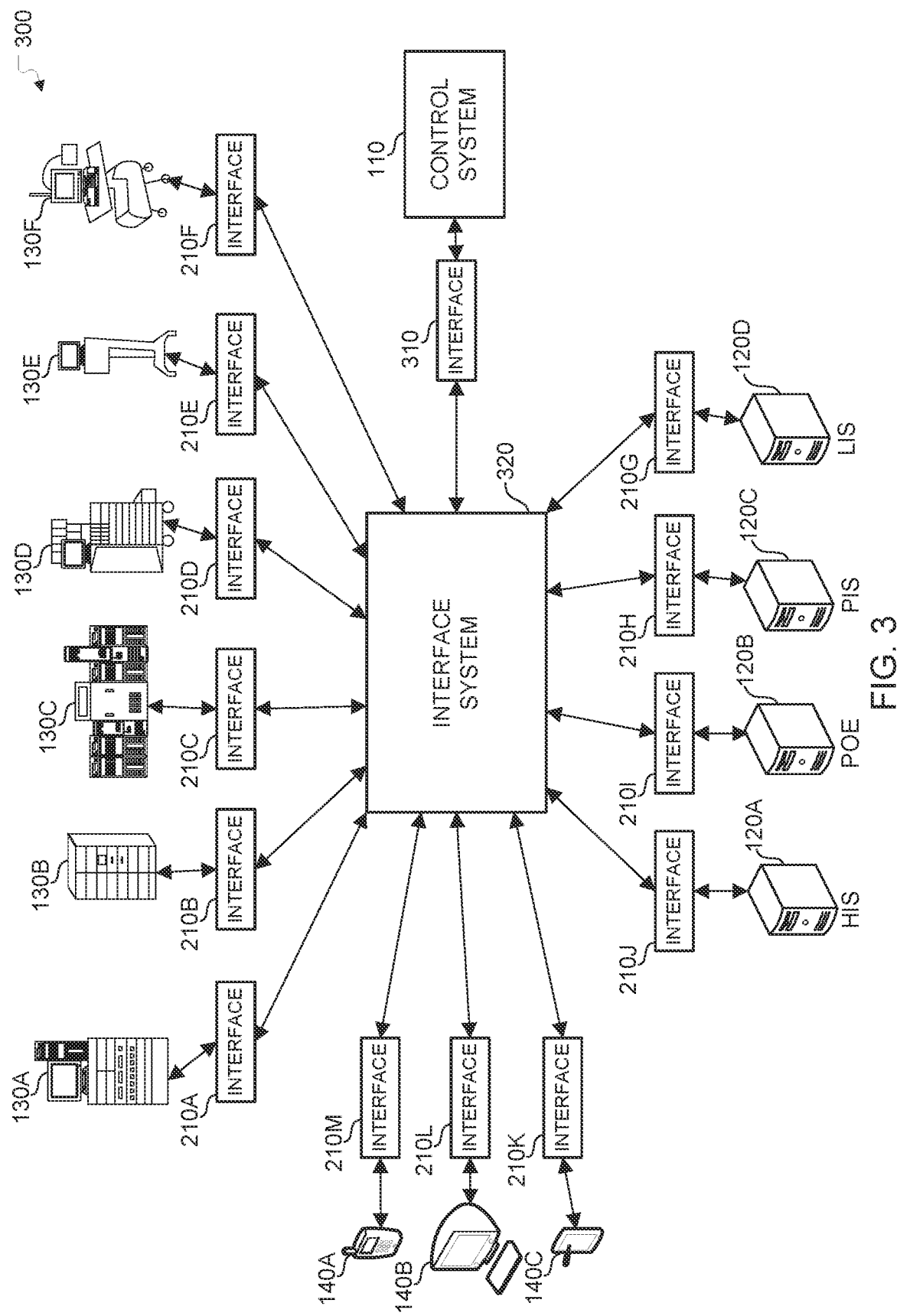
FIG. 3 illustrates an alternative example messaging architecture in which a context-aware healthcare notification system may be implemented in accordance with one or more embodiments.

FIG. 3 illustrates an alternative example messaging architecture 300 in which a context-aware healthcare notification system may be implemented in accordance with one or more embodiments. Not all of the depicted components may be required, however, and one or more embodiments may include additional components not shown in the figure. Variations in the arrangement and type of the components may be made without departing from the spirit or scope of the claims as set forth herein. Additional, different or fewer components may be provided.

The messaging architecture 300 includes an interface system 320, the control system 110, one or more healthcare systems 120A-D, one or more healthcare devices 130A-F, and one or more user devices 140A-C. The control system 110, interface system 320, healthcare systems 120A-D, healthcare devices 130A-F, and user devices 140A-C may be communicably coupled to one another, such as by the network 105 shown in FIG. 1. The one or more healthcare systems 120A-D, one or more healthcare devices 130A-F, and one or more user devices 140A-C may include, and/or may be coupled to, interfaces 210A-M. The control system 110 may include, and/or may be communicatively coupled to, the interface 310. The interfaces 210A-M, 310 may be adapters that are utilized by the one or more healthcare systems 120A-D, one or more healthcare devices 130A-F, one or more user devices 140A-C, and control system 110 to transmit messages to one another via the interface system 320. In one or more embodiments, the interfaces 210A-M, 310 may be, and/or may include, the adapters described in U.S. patent application Ser. No. 13/421,776, entitled "Scalable Communication System," filed on Mar. 15, 2012, which was previously incorporated by reference in its entirety for all purposes.

In the messaging architecture 300, the interface system 320 may be separate from the control system 110, e.g. such that messages to/from the control system 110 are routed through the interface system 320. For example, the control system 110 and the interface system 320 may be separate devices, such as separate servers, or the control system 110 and the interface system 320 may be and/or may include distinct hardware on the same device. Alternatively, the control system 110 may receive messages directly from the interface system 320, e.g. without the use of the interface 310. Thus, in the messaging architecture 300, messages are routed through the interface system 320, rather than through the control system 110, as previously discussed with respect to FIG. 2.

Alternatively, or in addition, one or more of the healthcare systems 120A-D, the healthcare devices 130A-F, the user devices 140A-C, and/or the control system 110 may communicate with the interface system 320 without utilizing the interfaces 210A-M, 310. Alternatively, or in addition, one or more of the healthcare systems 120A-D, the healthcare devices 130A-F, the user devices 140A-C, and/or the control system 110 may transmit messages directly to one another, e.g. without routing the messages through the interface system 320.

Figure 4:
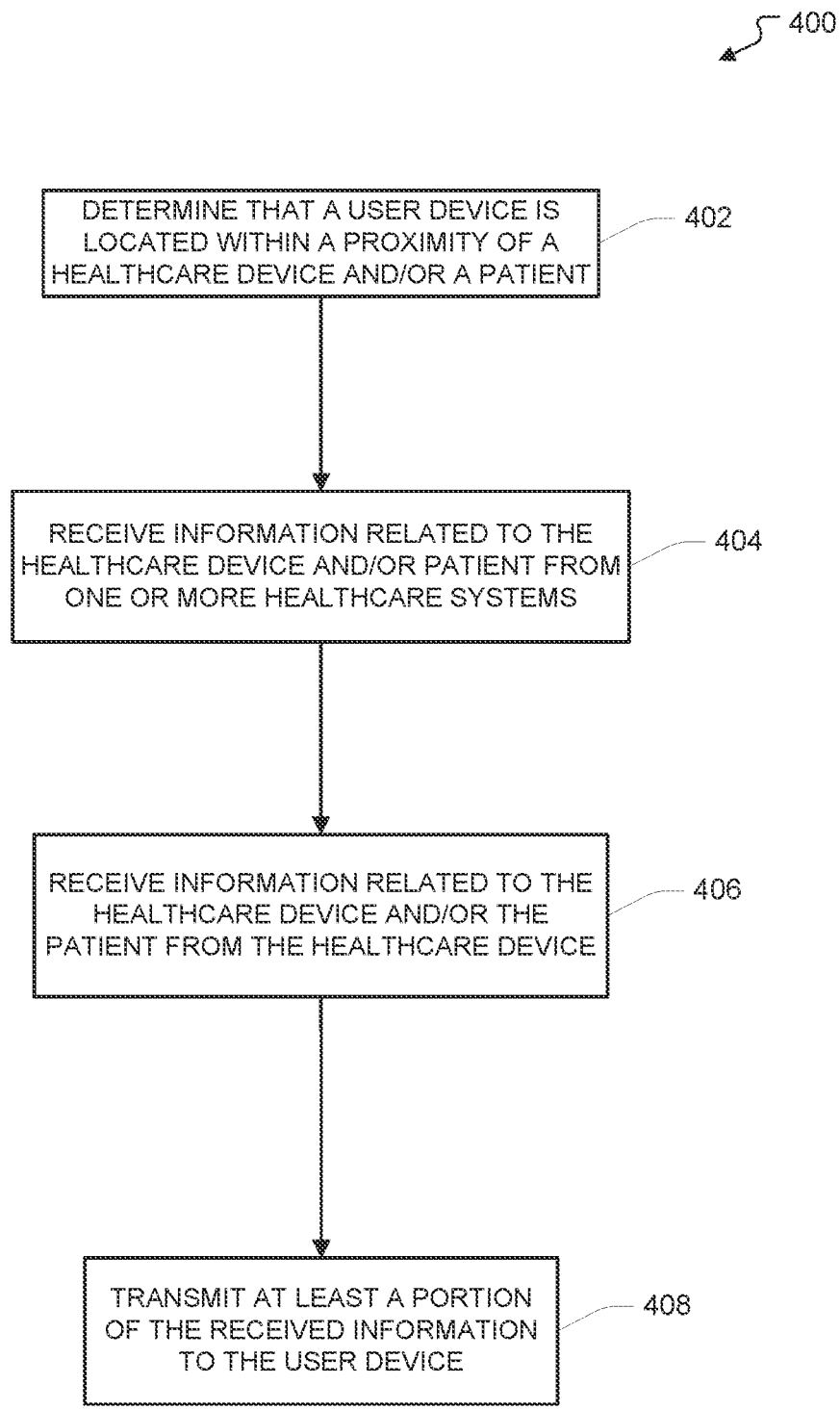
FIG. 4 illustrates a flow diagram of an example process for a context-aware healthcare notification system in accordance with one or more embodiments.

FIG. 4 illustrates a flow diagram of an example process 400 for a context-aware healthcare notification system in accordance with one or more embodiments. For explanatory purposes, the example process 400 is described herein with reference to the control system 110 of the example network environment 100 of FIG. 1; however, the example process 400 is not limited to the control system 110 of the example network environment 100 of FIG. 1. For example, in one or more embodiments the example process 400 may be performed by the interface system 320 of FIG. 3 and/or any of the healthcare systems 120A-D of FIG. 1. Further for explanatory purposes, the blocks of the example process 400 are described herein as occurring in serial fashion, or linearly. However, multiple blocks of the example process 400 may occur in parallel. In addition, the blocks of the example process 400 need not be performed in the order shown and/or one or more of the blocks of the example process 400 need not be performed.

In block 402, the control system 110 determines that one of the user devices 140A-C, such as the user device 140A, is located within a proximity of one of the healthcare devices 130A-F, such as the healthcare device 130A, and/or within a proximity of a patient, such as a patient for whom healthcare is being provided by, and/or facilitated by, one of the healthcare devices 130A-F, such as the healthcare device 130A. In one or more embodiments, the control system 110 may receive an indication from the user device 140A, and/or one or more of the healthcare devices 130A-F, indicating that the user device 140A is located within a proximity of one of the healthcare devices 130A-F and/or one or more patients. For example, the healthcare device 130A may be configured to determine when one of the user devices 140A-C is located within a proximity of the healthcare device 130A, e.g. by detecting one or more wireless signals transmitted by the user devices 140A-C, such as Infrared signals, wireless Ethernet signals, Bluetooth signals, or generally any wireless signals that are transmissible by the user devices 140A-C. Alternatively, or in addition, the healthcare device 130A may include an induction coil, and the healthcare device 130A may be configured to utilize the induction coil to determine whether the healthcare device 130A can interface with any of the user devices 140A-C.

Alternatively, or in addition, the control system 110 may determine that the user device 140A is located within a proximity of the healthcare device 130A based at least in part on information and/or signals that are received, directly or indirectly, from the user device 140A and/or the healthcare device 130A. For example, the control system 110 may utilize triangulation or other positioning techniques to determine the locations of the user device 140A and/or the healthcare device 130A based on wireless signals received from the user device 140A and/or the healthcare device 130A. Alternatively, or in addition, the control system 110 may receive information from one or more of the healthcare systems 120A-D that indicates the location of the healthcare device 130A, such as over the network 105. The control system 110 may then determine the location of the user device 140A and/or whether the user device 140A is located within a proximity of the location of the healthcare device 130A.

In one or more embodiments, the healthcare device 130A may store an identifier of a patient for whom the healthcare device 130A is providing healthcare, and/or facilitating with providing healthcare. Thus, the healthcare device 130A may provide the control system 110 with an identifier of a patient that may be located within a proximity of the user device 140A, e.g. when the healthcare device 130A is located within the proximity of the user device 140A. Alternatively, or in addition, the control system 110 may retrieve an identifier of the patient for whom the healthcare device 130A is providing, and/or facilitating with providing, healthcare from one or more of the healthcare systems 140A-D.

In one or more embodiments, the patients may be provided with a patient information device, such as a wristband, necklace, ankle band, etc., that may be, or may include, an active embedded computer and/or a passive device, such as a radio frequency identification device. The patient information device may be responsive to devices located throughout the healthcare facility, such as readers or wireless transmitter/receivers, to provide the identity of the patient associated with the patient information device, and/or other information, when the patient information device is queried, e.g. activated, by the devices. In one or more embodiments, any of the healthcare devices 130A-F, and/or any of the user devices 140A-C, may include the devices that query, e.g. activate, the patient information device and receive the patient identifiers from the patient information devices.

Thus, in one or more embodiments, the devices that are located throughout the hospital may receive identifiers of proximally located patients, e.g. patients that are located within a proximity of the devices, and the devices may transmit the identifiers of the patients to the control system 110, such as over the network 105. The control system 110 may retrieve the locations of the devices from one or more of the healthcare systems 120A-D, such as a hospital information system, and the control system 110 may determine the approximate locations of the patients based on the location of the devices that transmitted the identifiers of the patients. The control system 110 may then determine whether any of the user devices 140A-C are located within a proximity of the approximate locations of any of the patients.

In block 404, the control system 110 may receive information from one or more of the healthcare systems 120A-D that is related to the healthcare device 130A that is located within a proximity of the user device 140A, and/or that is related to any patients that are located within a proximity of the user device 140A. For example, the control system 110 may receive information from one or more of the healthcare systems 120A-D over the network 105. In one or more embodiments, the received information may include information regarding medications being provided to a patient, such as from the pharmacy information system, lab results for a patient, such as from a laboratory information system, a medical history and/or profile of the patient, such as from the pharmacy information system and/or a hospital information system, the status of medications being prepared for the patient, such as from a pharmacy information system, maintenance and/or calibration information related to the healthcare device 130A, and/or generally any information that may be provided by any of the healthcare systems 120A-D. In one or more embodiments, the control system 110 may not receive any information from any of the healthcare systems 120A-D, e.g. the control system 110 may, in one or more embodiments, skip block 404.

In block 406, the control system 110 may receive information from the healthcare device 130A that is located within a proximity of the user device 140A. The received information may be related to the healthcare device 130A, and/or the received information may be related to any patients that are located within a proximity of the user device 140A. For example, the control system 110 may receive information from the healthcare device 130A over the network 105. In one or more embodiments, the information may include information related to the progress of delivering a medication to a patient, such as from an infusion pump, information related to the monitoring of a vital sign of a patient, such as from a monitoring device, information related to the progress of a respiratory protocol being implemented for the patient, such as from a respiratory device, or generally any information that may be received from the healthcare device 130A. In one or more embodiments, the control system 110 may not receive any information from the healthcare device 130A, e.g. the control system 110 may, in one or more embodiments, skip block 406.

In block 408, the control system 110 transmits at least a portion of the information received from one or more of the healthcare systems 120A-D, and/or the healthcare device 130A, to the user device 140A. For example, the control system 110 may transmit at least a portion of the received information to the user device 140A over the network 105. In one or more embodiments, the user device 140A may display the at least the portion information, e.g. to a healthcare professional, such as a physician or a nurse, as is discussed further below with respect to FIGS. 5-6.

Alternatively, or in addition, the control system 110 may process the information received from the one or more healthcare systems 120A-D, and/or the healthcare device 130A, such as to generate workflow information, control information, or other information that can be generated from processing the received information. The control system 110 may then transmit the processed information, and/or the information generated at least in part from processing the received information, to the user device 140A. For example, the control system 110 may process the received information to determine whether any corrective actions are required, any safety issues exists, and/or any errors exists. If the control system 110 determines that any corrective actions are required, any safety issues exists, and/or any errors exists, the control system 110 may transmit an indication of the corrective action, the safety issue, and/or the error to the user device 140A, such as via an alert and/or notification.

In one or more embodiments, the control system 110 may process the information received from the one or more healthcare systems 120A-D, and/or the healthcare device 130A, in addition to information received from the user device 140A, in order to provide context to an alert and/or notification. The control system 110 may utilize information such as the proximity of the user device 140A to the healthcare device 130A, a condition of a patient whom the healthcare device 130A is providing healthcare, a type of medication being administered to the patient, or generally any other received information, to provide context to an alert and/or notification. For example, if the processed information indicates that a healthcare professional is standing next to the healthcare device 130A, then the control system 110 may cause a visual alert to be displayed to the healthcare professional, rather than an audible alert. Similarly, if the processed information indicates, e.g., that medication on an infusion pump is not life critical, then the control system 110 may provide a notification to a healthcare professional who is caring for the patient but is located remotely from the infusion pump, rather than any healthcare professional who is located proximally to the infusion pump.

Alternatively, or in addition, the control system 110 may delay alarms on the healthcare devices 130A-F, and/or may allow a healthcare professional to indicate that they will respond to an alarm within a configurable amount of time. For example, if a healthcare professional indicates that they will respond to an alarm of a healthcare device 130A within a configurable amount of time, the control system 110 may cause the healthcare device 130A to not generate the alarm unless the configurable amount of time has elapsed and the healthcare professional has not responded to the alarm.

In one or more embodiments, a healthcare professional may remotely determine, such as via one of the user devices 140A-C, that an action should be taken by a pump, such as restarting the pump when the volume counts down to zero, and adding a small amount of volume to allow the infusion to restart and to provide an associated nurse with a more convenient time to address the infusion, e.g. to change to a new bag. Thus, a healthcare professional may be able to address an alarm of a healthcare device 130A remotely, such as via one of the user devices 140A-C. Alternatively, or in addition, the control system 110, and/or a drug library, may store actions that may be taken remotely, e.g. via one of the user devices 140A-C, based on characteristics of the healthcare device 130A, the patient, the alarm, etc. For example, the control system 110 may allow different actions to be performed remotely, via reprogramming a healthcare device 130A, based on one or more of: the type of drug being administered by the healthcare device 130A, the type of alarm being generated by the healthcare device 130A, the patient care area where the healthcare device 130A is located, and/or generally any characteristics associated with the healthcare device 130A and/or the patient.

Figure 5:
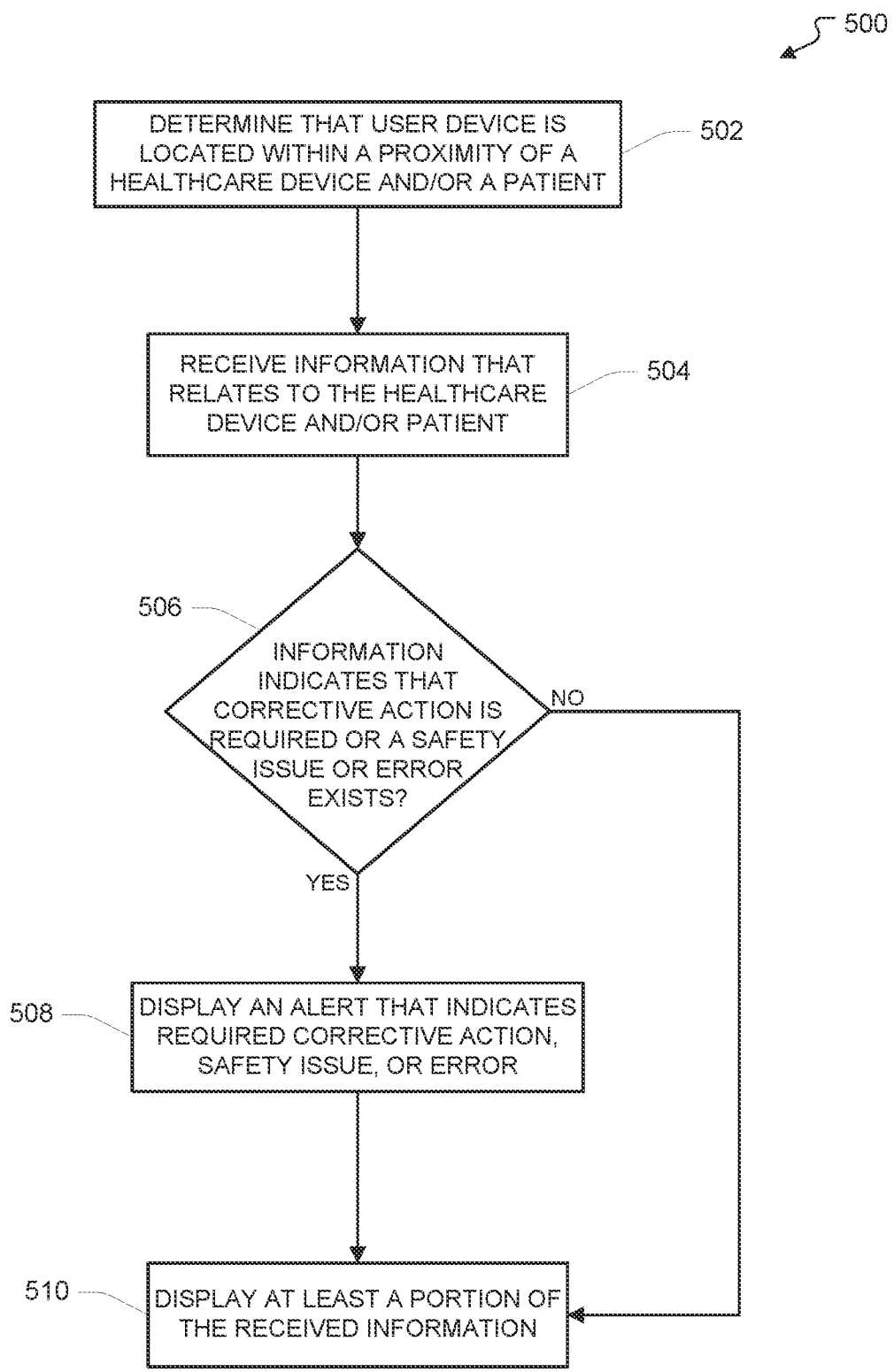
FIG. 5 illustrates a flow diagram of an example process for a user device in a context-aware healthcare notification system in accordance with one or more embodiments.

FIG. 5 illustrates a flow diagram of an example process 500 for a user device 140A in a context-aware healthcare notification system in accordance with one or more embodiments. For explanatory purposes, the example process 500 is described herein with reference to the user device 140A of the example network environment 100 of FIG. 1: however, the example process 500 is not limited to the user device 140A of the example network environment 100 of FIG. 1. Further for explanatory purposes, the blocks of the example process 500 are described herein as occurring in serial fashion, or linearly. However, multiple blocks of the example process 500 may occur in parallel. In addition, the blocks of the example process 500 need not be performed in the order shown and/or one or more of the blocks of the example process 500 need not be performed.

In block 502, a user device 140A determines that it is located within a proximity of a healthcare device and/or a patient. For example, the user device 140A may include a device that is configured to query patient information devices that, for example, may be worn by patients. Thus, the user device 140A may determine that it is located within a proximity of a patient when the user device 140A receives a response from a queried patient information device of a patient. In one or more embodiments, the user device 140A may determine that it is located within a proximity of a healthcare device 130A based on wireless signals received from the healthcare device 130A, and/or a device or wireless interface coupled thereto. The wireless signals may include, e.g., Infrared signals, Bluetooth signals, wireless Ethernet signals, and/or generally any wireless signals. For example, the user device 140A may measure the strength of a signal received from the healthcare device 130A, such as for a wireless Ethernet signal and/or other long range wireless signals, and/or the user device 140A may determine whether it receives any signal from the healthcare device 130A, such as for Infrared signals, Bluetooth signals, and/or other short range wireless signals. In one or more embodiments, the user device 140A may include an induction coil that may be utilized by the user device 140A to determine whether the user device 140A can interface with the healthcare device 130A, such as via radio frequency identification. The user device 140A may transmit an indication to the control system 110, the interface system 320, and/or any of the healthcare systems 120A-D, when the user device 140A determines that it is located within a proximity of the healthcare device 130A.

Alternatively, or in addition, the user device 140A may receive an indication from the control system 110, the healthcare device 130A, the interface system 320, and/or any of the healthcare systems 120A-D, that indicates that the user device 140A is located within a proximity of the healthcare device 130A and/or one or more patients. In this instance, the user device 140A may determine that it is located within a proximity of the healthcare device 130A and/or the one or more patients based at least in part on the received indication.

In block 504, the user device 140A receives information that relates to the proximally located healthcare device 130A and/or the one or more proximally located patients. For example, the user device 140A may receive the information from the control system 110, such as over the network 105. Alternatively, or in addition, the user device 140A may receive the information from one or more of the healthcare systems 120A-D and/or the interface system 320, such as over the network 105.

In block 506, the user device 140A determines whether the received information indicates that corrective action is required, a safety issue exists, or an error exists with respect to the healthcare device 130A and/or the one or more proximally located patients. In one or more embodiments, the control system 110 may determine that corrective action is required, a safety issue exists, and/or an error exists, and the received information may indicate the corrective action, safety issue and/or error determined by the control system 110, such as a safety issue or error with respect to delivery protocols, drug interactions, etc.

If, in block 506, the user device 140A determines that corrective action is required, a safety issue exists, and/or an error exists, the user device 140A moves to block 508. In block 508, the user device 140A displays an alert, or notification, that indicates the required corrective action, safety issue, and/or error. For example, the user device 140A may display a graphical indicator to indicate the existence of a required corrective action, a safety issue, or an error, with respect to the healthcare device 130A and/or the one or more proximally located patients, such as the asterisk ("*") indicator discussed below with respect to FIGS. 7 and 10.

If, in block 506, the user device 140A determines that the received information does not indicate that a corrective action is required, a safety issue exists, and/or an error exists, the user device 140A moves to block 510. In block 510, the user device 140A displays at least a portion of the received information. For example, the user device 140A may display at least a portion of the received information via one or more of the user interfaces that are discussed further below with respect to FIGS. 7-10.

Alternatively, or in addition, the user device 140A may not display the at least the portion of the received information until prompted by a user, such as a healthcare professional interacting with the user device 140A. For example, the user device 140A may display a notification to the healthcare professional that indicates that the received information is available, and that requests whether the healthcare professional would like the user device 140A to display the at least the portion of the received information on a screen of the user device 140A, and/or on a display or monitor proximally located to the user device 140A.

Figure 6:
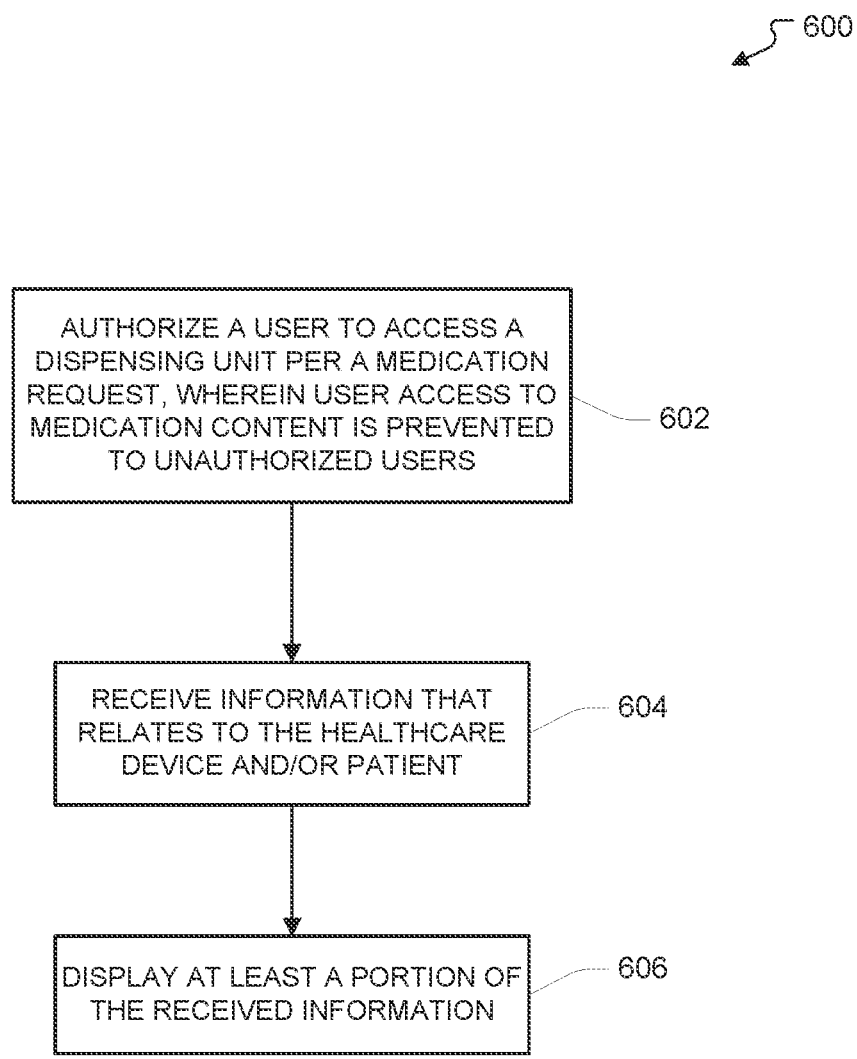
FIG. 6 illustrates a flow diagram of an example process for a user device in a context-aware healthcare notification system in accordance with one or more embodiments.

FIG. 6 illustrates a flow diagram of an example process 600 for a user device 140A in a context-aware healthcare notification system in accordance with one or more embodiments. For explanatory purposes, the example process 600 is described herein with reference to the user device 140A of the example network environment 100 of FIG. 1; however, the example process 600 is not limited to the user device 140A of the example network environment 100 of FIG. 1. Further for explanatory purposes, the blocks of the example process 600 are described herein as occurring in serial fashion, or linearly. However, multiple blocks of the example process 600 may occur in parallel. In addition, the blocks of the example process 600 need not be performed in the order shown and/or one or more of the blocks of the example process 600 need not be performed.

In block 602, the user device 140A receives an indication that it is located within a proximity of a healthcare device 130A and/or of one or more patients. For example, the user device 140A may receive the indication from the control system 110, the healthcare device 130A, the interface system 320, and/or any of the healthcare systems 120A-D, such as over the network 105. In one or more embodiments, the indication may be a wireless signal generated by the healthcare device 130A, and/or a device that is communicatively coupled thereto, that is detected by the user device 140A, such as an Infrared signal, a Bluetooth signal, a radio frequency identification signal, or generally any wireless signal.

In block 604, the user device 140A receives information that relates to the healthcare device 130A and/or the one or more proximally located patients. As previously discussed, the user device 140A may, e.g., receive the information from one or more of the control system 110, the healthcare systems 120A-D, and/or the interface system 320, such as over the network 105.

In block 606, the user device 140A may display at least a portion of the received information, such as via one or more of the user interfaces that are discussed below with respect to FIGS. 7-10. In one or more embodiments, a user interacting with the user device 140A, such as a healthcare professional, may utilize the displayed information to facilitate with providing healthcare to a patient. For example, the healthcare professional may utilize the user interface to adjust a parameter associated with providing healthcare to the patient, such as a rate at which a medication is being administered to the patient by the healthcare device 130A, the scheduled time that a medication will be prepared for the patient by the pharmacy, e.g. via the pharmacy information system, or generally any parameter that relates to providing healthcare to the patient that may be configurable via the user device 140A, such as over the network 105.

Figure 7:
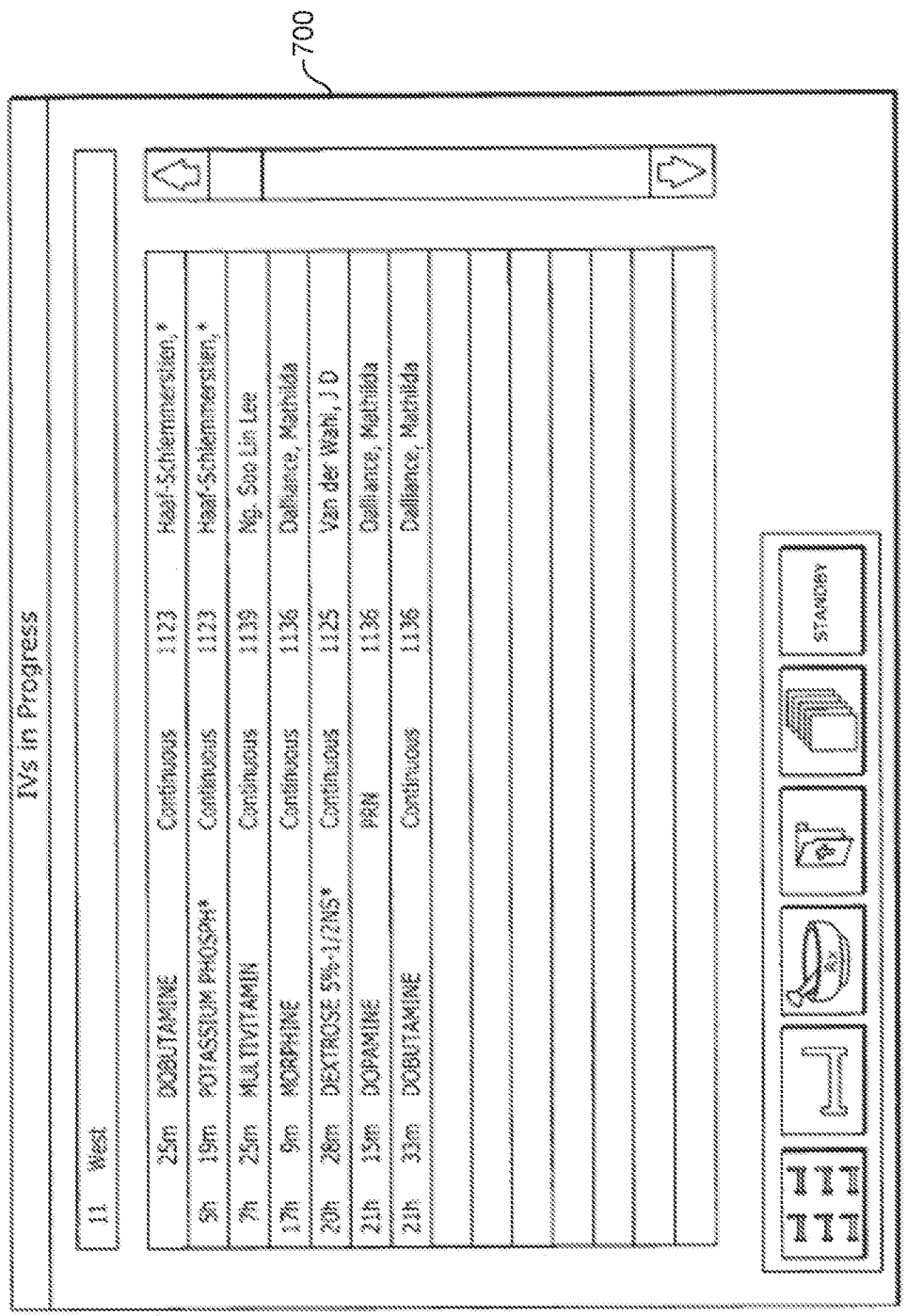
FIG. 7 illustrates an example user interface that may be implemented in a context-aware healthcare notification system in accordance with one or more embodiments.

FIG. 7 illustrates an example user interface 700 that may be implemented in a context-aware healthcare notification system in accordance with one or more embodiments. Not all of the depicted components may be required, however, and one or more embodiments may include additional components not shown in the figure. Variations in the arrangement and type of the components may be made without departing from the spirit or scope of the claims as set forth herein. Additional, different or fewer components may be provided.

The user interface 700 may display information relating to in-progress actions being performed by one or more of the healthcare devices 130A-F, such as medical orders being administered. For example, the user interface 700 displays a report of IVs that are being administered by, and/or with the facilitation of, one or more of the healthcare devices 130A-F. In one or more embodiments, the administrations of medical orders that will terminate within a preselected time period may be distinguished on the user interface 700 from other administrations by color highlighting or other means. The user interface 700 may further display the time remaining, medication, and patient name, as well as buttons for program control. In one or more embodiments, the user interface 700 may display pending infusions or infusions scheduled to begin within a preselected time period.

In operation, the user interface 700 may be provided by the control system 110, and/or one or more of the healthcare systems 120A-D, for display on a screen, such as a screen of one or more of the user devices 140A-C, and/or a screen or monitor associated with one or more of the healthcare systems 120A-D. For example, the control system 110 may receive messages from one or more of the healthcare devices 130A-F related to actions being performed by the one or more healthcare devices 130A-F. The control system 110 may parse the received messages to obtain the information displayed on the user interface 700, and/or the received messages may be displayed on the user interface 700.

The information displayed on the user interface 700 may be updated in real-time as the control system 110 and/or one or more of the healthcare systems 120A-D receives messages from the healthcare devices 130A-F, such as while orders are being administered to patients. In one or more embodiments, the user interface 700 may be used to modify the preparation of medications, such as by scheduling and/or rescheduling, the preparation of medications.

In one or more embodiments, the user interface 700 may also display notifications, and/or alerts, such as when a healthcare professional is associated with a user device 140A that is displaying the user interface 700. For example, in the user interface 700, the notifications may be indicated by an asterisk ("*"). In one or more embodiments, the healthcare professional may select information that is displayed with an asterisk, such as by touching or clicking on the information, to receive additional information regarding the notification. In one or more embodiments, one or more of the alerts and/or notifications may only be displayed when the healthcare professional is proximally located to the one or more healthcare devices 130A-F to which the alerts and/or notifications pertain.

Figure 8:
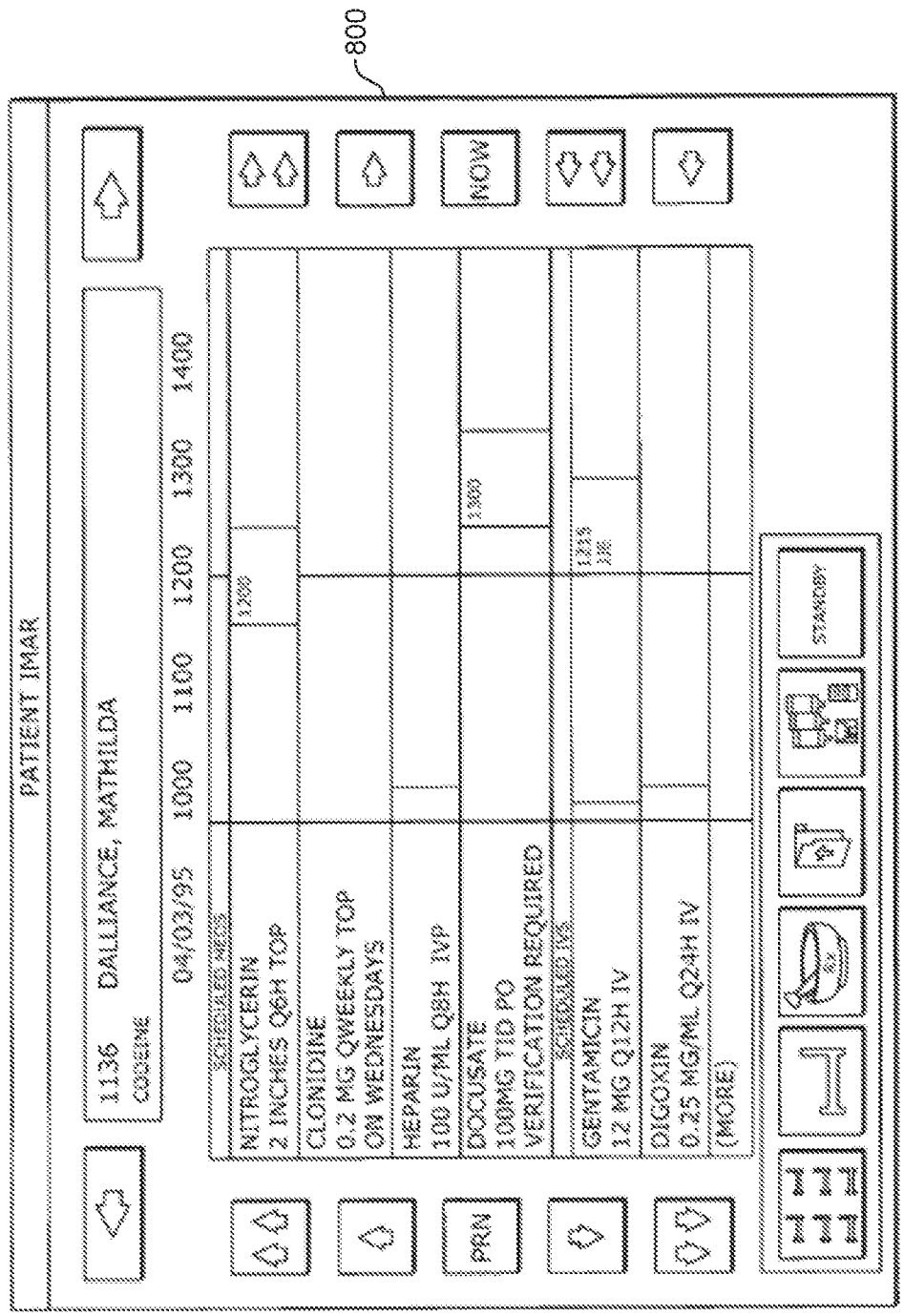
FIG. 8 illustrates an example user interface that may be implemented in a context-aware healthcare notification system in accordance with one or more embodiments.

FIG. 8 illustrates an example user interface 800 that may be implemented in a context-aware healthcare notification system in accordance with one or more embodiments. Not all of the depicted components may be required, however, and one or more embodiments may include additional components not shown in the figure. Variations in the arrangement and type of the components may be made without departing from the spirit or scope of the claims as set forth herein. Additional, different or fewer components may be provided.

The user interface 800 may display information relating to a patient, such as information received from one or more of the healthcare systems 120A-C and/or one or more of the healthcare devices 130A-F. The displayed information may include information related to medications and/or infusions, such as IVs, that are scheduled for the patient, and the information may be received from the healthcare system 120C. The information may further include information related to medications and/or infusions that are being administered to the patient, and this information may be received from one or more of the healthcare devices 130A-F. For example, the user interface 800 displays information related to scheduled medications and IVs for an identified patient. In one or more embodiments, the user interface 800 may be color coded to indicate the status and schedule of each medication administration. For example, a medication delivery window extending from thirty minutes prior and thirty minutes after the scheduled administration time may be indicated by a yellow band on the user interface 800.

In operation, the user interface 800 may be provided by the control system 110, and/or one or more of the healthcare systems 120A-D, for display on a screen, such as a screen of one or more of the user devices 140A-C, and/or a screen or monitor associated with one or more of the healthcare systems 120A-D. For example, the control system 110 may receive messages from one or more of the healthcare systems 120A-D, and/or one or more of the healthcare devices 130A-F, that relate to a patient. The control system 110 may parse the received messages to obtain the information displayed on the user interface 800, and/or the received messages may be displayed on the user interface 800.

In one or more embodiments, the user interface 800 may automatically be provided to the user device 140A of a healthcare professional when the healthcare professional is located within a proximity of the patient and/or within a proximity of one or more healthcare devices 130A-F that are providing, and/or facilitating with providing, healthcare to the patient. Thus, the user device 140A of a healthcare professional may automatically display, and/or prepare for display, information related to an identified patient when the healthcare professional is within proximity of the patient, such as at the bedside of the patient. Accordingly, the information displayed on the user interface 800 may change as the healthcare professional moves throughout the healthcare facility.

In one or more embodiments, the user device 140A may receive information for displaying the user interface 800 when the healthcare professional is proximally located to the patient, but the user device 140A may not display the user interface 800 until prompted by the healthcare professional. For example, the user device 140A may receive the information for displaying the user interface 800 and may then display a notification to the healthcare professional indicating that the information is available, and requesting whether the healthcare professional would like the user interface 800 to be displayed on the user device 140A and/or on a display or monitor proximally located to the user device 140A.

The information displayed on the user interface 800 may be updated in real-time as the control system 110 and/or one or more of the healthcare systems 120A-D receives messages from the healthcare devices 130A-F, such as while orders are being administered to the patient. In one or more embodiments, the user interface 800 may be used to schedule and/or reschedule, the preparation of medications, such as by the healthcare system 120C.

The information displayed on the user interface 800 may be updated in real-time as the control system 110 and/or one or more of the healthcare systems 120A-D receives messages from the healthcare devices 130A-F and/or the healthcare systems 120A-D, such as while orders are being administered to patients, while orders are being prepared for administration to patients, and/or when orders are received from a physician order entry system. In one or more embodiments, the user interface 800 may be used to verify the administration of orders, such as a healthcare professional verifying that a medication scheduled for administration and/or a medication being administered coincides with the ordered medication. In one or more embodiments, a healthcare professional may be able to select, such as touch or click on, an order and the user interface 800 may display a picture of the medication being administered, or about to be administered.

Figure 9:
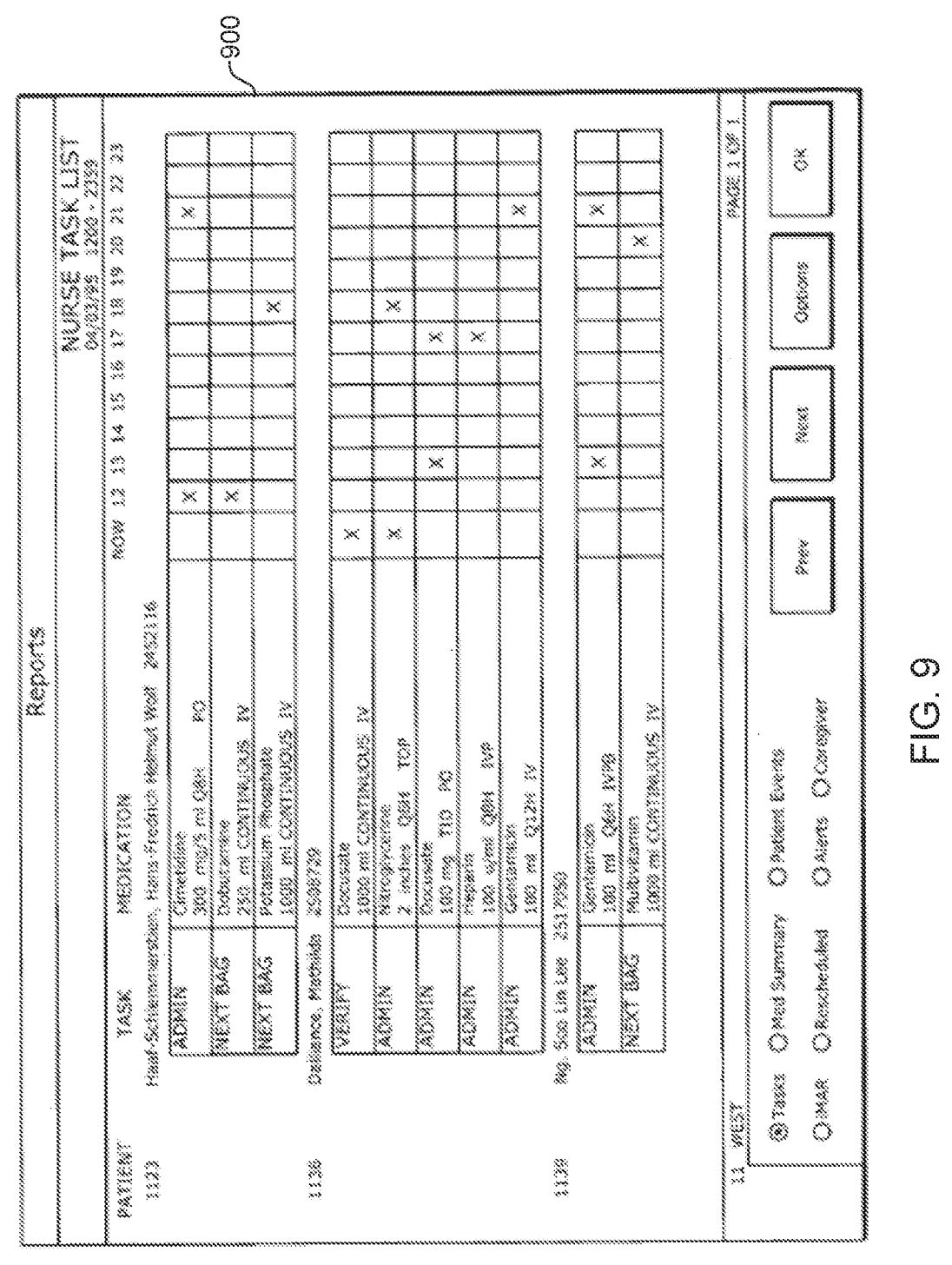

FIG. 9 illustrates an example user interface 900 that may be implemented in a context-aware healthcare notification system in accordance with one or more embodiments. Not all of the depicted components may be required, however, and one or more embodiments may include additional components not shown in the figure. Variations in the arrangement and type of the components may be made without departing from the spirit or scope of the claims as set forth herein. Additional, different or fewer components may be provided.

The user interface 900 may display information to an identified healthcare professional that relates to in-progress actions being performed by, and/or with the facilitation of, one or more of the healthcare devices 130A-F, and for which the healthcare professional is facilitating and/or monitoring. The user interface 900 may also display information to the identified healthcare professional that relates to future actions to be performed by, and/or with the facilitation of, one or more of the healthcare devices 130A-F, and for which the healthcare professional is facilitating and/or monitoring. Alternatively, or in addition, the user interface 900 may display information related to in-progress or future actions that are being performed proximally to the user device 140A, and a healthcare professional accessing the user device 140A. For example, the user interface 900 displays a report of IVs that are being administered by one or more of the healthcare devices 130A-F. In one or more embodiments, the user interface 900 may include scheduling of medication administrations to ensure proper medication of the patient while distributing the workload over a period of time to ensure that all medication is given promptly.

In operation, the user interface 900 may be provided by the control system 110, and/or one or more of the healthcare systems 120A-D, for display on a screen, such as a screen of one or more of a user devices 140A being accessed by a healthcare professional, and/or a screen or monitor associated with one or more of the healthcare systems 120A-D. For example, the control system 110 may receive messages from one or more of the healthcare systems 120A-D, and/or one or more of the healthcare devices 130A-F, that relate to in-progress actions and/or future actions that are being performed with the facilitation of the healthcare professional, and/or that are being performed proximally to the healthcare professional, as indicated by the location of the user device 140A. The control system 110 may parse the received messages to obtain the information displayed on the user interface 900, and/or the received messages may be displayed on the user interface 900.

In one or more embodiments, the user interface 900 may automatically be provided to the user device 140A of a healthcare professional when the healthcare professional is located within a proximity of the patient and/or within a proximity of one or more healthcare devices 130A-F that are providing, and/or facilitating with providing, healthcare to one or more patients. Thus, the user device 140A of a healthcare professional may automatically display, and/or prepare for display, information related to in-progress and/or future actions that are being performed, and/or will be performed, proximally to the location of the healthcare professional. Accordingly, the information displayed on the user interface 900 may change as the healthcare professional moves throughout the healthcare facility.

In one or more embodiments, the user device 140A may receive information for displaying the user interface 900 when the healthcare professional is proximally located to in-progress, or future actions, but the user device 140A may not display the user interface 900 until prompted by the healthcare professional. For example, the user device 140A may receive the information for displaying the user interface 900 and may then display a notification to the healthcare professional indicating that the information is available, and requesting whether the healthcare professional would like the user interface 900 to be displayed on the user device 140A and/or on a display or monitor proximally located to the user device 140A.

The information displayed on the user interface 900 may be updated in real-time as the control system 110 and/or one or more of the healthcare systems 120A-D receives messages from the healthcare devices 130A-F, such as while orders are being administered to patients. In one or more embodiments, the user interface 900 may be used to verify the administration of orders, such as a healthcare professional verifying that a medication scheduled for administration and/or a medication being administered coincides with the ordered medication. In one or more embodiments, a healthcare professional may be able to select, such as touch or click on, an order and the user interface 900 may display a picture of the medication being administered, or about to be administered.

Figure 10:
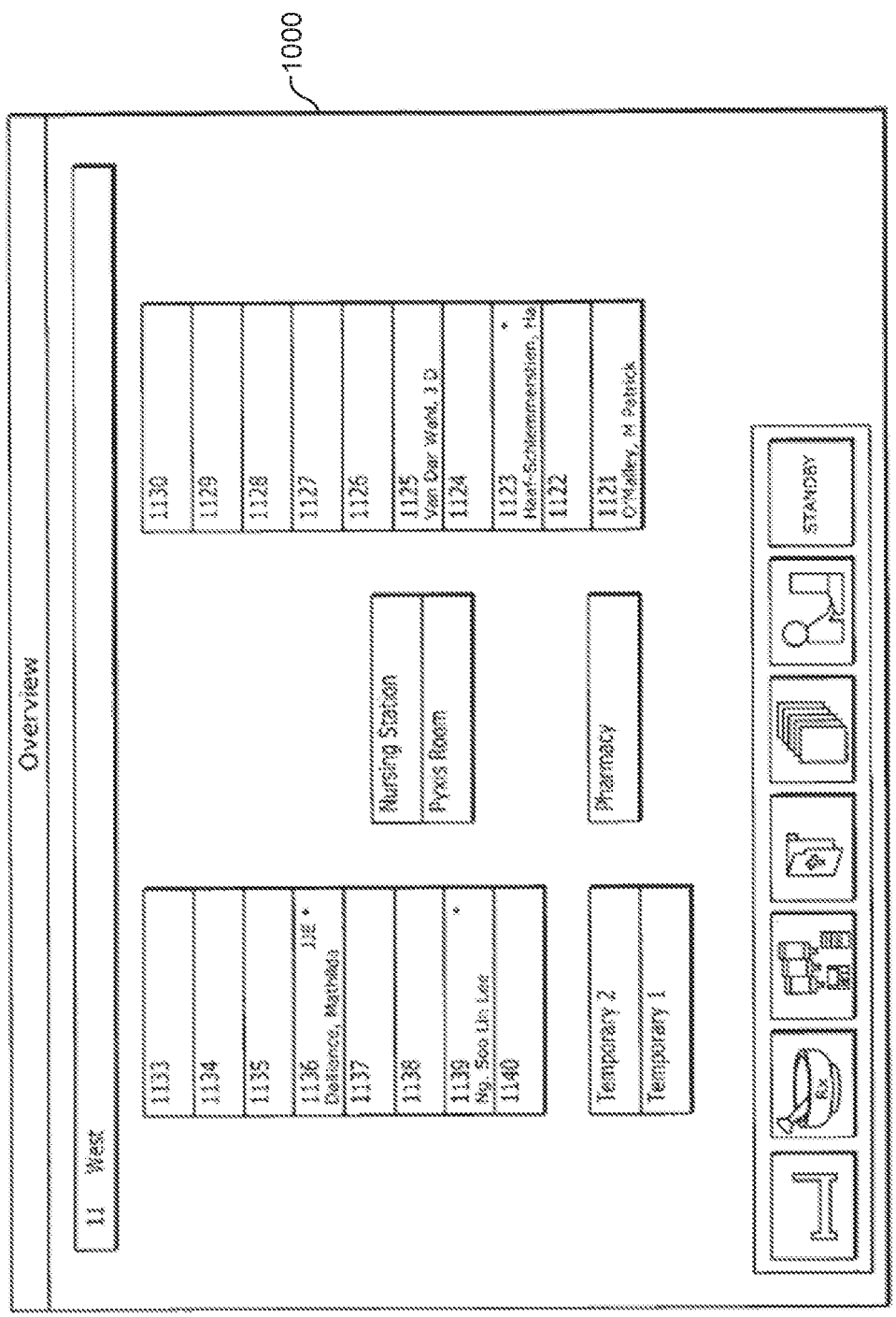
FIG. 10 illustrates an example user interface that may be implemented in a context-aware healthcare notification system in accordance with one or more embodiments.

FIG. 10 illustrates an example user interface 1000 that may be implemented in a context-aware healthcare notification system in accordance with one or more embodiments. Not all of the depicted components may be required, however, and one or more embodiments may include additional components not shown in the figure. Variations in the arrangement and type of the components may be made without departing from the spirit or scope of the claims as set forth herein. Additional, different or fewer components may be provided.

The user interface 1000 may display information relating to patients in a healthcare facility and/or in an area of a healthcare facility, such as alerts or notifications related to healthcare being administered to patients in a healthcare facility. For example, the user interface 1000 may display a graphical representation of each room in an area of the healthcare facility, the name of the patient occupying each room, if any, and any alerts or notifications that apply to any of the displayed patients. In the user interface 1000, an alert or notification is indicated by an asterisk ("*"); however, any other graphical indicator may be used to indicate an alert and/or notification.

In operation, the user interface 1000 may be provided by the control system 110, and/or one or more of the healthcare systems 120A-D, for display on a screen, such as a screen of one or more of the user devices 140A-C, and/or a screen or monitor associated with one or more of the healthcare systems 120A-D. For example, the control system 110 may receive messages from one or more of the healthcare devices 130A-F related to actions being performed by the or more healthcare devices 130A-F. The control system 110 may parse the received messages to determine whether any alerts and/or notifications should be displayed via the user interface 1000, such as whether any discrepancies and/or errors are identified from the received messages.

In one or more embodiments, the user interface 1000 may automatically be provided to the user device 140A of a healthcare professional when the healthcare professional is located within a proximity of the area of the healthcare facility represented on the user interface 1000. Thus, the user device 140A of a healthcare professional may automatically display, and/or prepare for display, the user interface 1000 when a healthcare professional is proximally located to the represented area. Accordingly, the information displayed on the user interface 1000 may change as the healthcare professional moves throughout the healthcare facility.

In one or more embodiments, the user device 140A may receive information for displaying the user interface 1000 when the healthcare professional is located proximally to the represented area, but the user device 140A may not display the user interface 1000 until prompted by the healthcare professional. For example, the user device 140A may receive the information for displaying the user interface 1000 and may then display a notification to the healthcare professional indicating that the information is available, and requesting whether the healthcare professional would like the user interface 1000 to be displayed on the user device 140A and/or on a display or monitor proximally located to the user device 140A.

The information displayed on the user interface 1000 may be updated in real-time as the control system 110 and/or one or more of the healthcare systems 120A-D receives messages from the healthcare devices 130A-F, such as while orders are being administered to patients.

In one or more embodiments, the user interface 1000 may display the status of each patient's infusion, and when an alert occurs, the box representing the patient's room flashes red to attract attention to the alert. Accordingly, a healthcare professional accessing the user interface 1000 may be able to quickly and easily identify the patient from the user interface, such as at a nursing station, and take appropriate action to address the condition causing the alert. In one or more embodiments, certain alerts that have been identified as particularly important events may be displayed on multiple screens throughout the healthcare facility, such as in the pharmacy.

In one or more embodiments, the user interface 1000 may also be used for updating administrative records of the healthcare facility. For example, if a patient changes rooms, a healthcare professional can transmit a notification of the room change to the control system 110 by selecting the patient's name, and dragging that patient to the new room. In addition, the user interface 1000 may be updated to reflect the room change.

FIG. 11 conceptually illustrates electronic system 1100 with which one or more embodiments of the subject technology may be implemented. Electronic system 1100, for example, can be, or can include, the control system 110, the interface system 320, one or more of the healthcare systems 120A-D, one or more of the healthcare devices 130A-F, one or more of the user devices 140A-C, a desktop computer, a laptop computer, a tablet computer, a phone, a personal digital assistant (PDA), and/or generally any electronic device that transmits signals over a network. Such an electronic system includes various types of computer readable media and interfaces for various other types of computer readable media. Electronic system 1100 includes bus 1108, processing unit(s) 1112, system memory 1104, read-only memory (ROM) 1110, permanent storage device 1102, input device interface 1114, output device interface 1106, and network interface 1116, or subsets and variations thereof.

Bus 1108 collectively represents all system, peripheral, and chipset buses that communicatively connect the numerous internal devices of electronic system 1100. In one or more embodiments, bus 1108 communicatively connects processing unit(s) 1112 with ROM 1110, system memory 1104, and permanent storage device 1102. From these various memory units, processing unit(s) 1112 retrieves instructions to execute and data to process in order to execute the processes of the subject disclosure. The processing unit(s) can be a single processor or a multi-core processor in different embodiments.

ROM 1110 stores static data and instructions that are needed by processing unit(s) 1112 and other modules of the electronic system. Permanent storage device 1102, on the other hand, is a read-and-write memory device. This device is a non-volatile memory unit that stores instructions and data even when electronic system 1100 is off. One or more embodiments of the subject disclosure use a mass-storage device (such as a magnetic or optical disk and its corresponding disk drive) as permanent storage device 1102.

Other embodiments use a removable storage device (such as a floppy disk, flash drive, and its corresponding disk drive) as permanent storage device 1102. Like permanent storage device 1102, system memory 1104 is a read-and-write memory device. However, unlike storage device 1102, system memory 1104 is a volatile read-and-write memory, such as random access memory. System memory 1104 stores any of the instructions and data that processing unit(s) 1112 needs at runtime. In one or more embodiments, the processes of the subject disclosure are stored in system memory 1104, permanent storage device 1102, and/or ROM 1110. From these various memory units, processing unit(s) 1112 retrieves instructions to execute and data to process in order to execute the processes of one or more embodiments.

Bus 1108 also connects to input and output device interfaces 1114 and 1106. Input device interface 1114 enables a user to communicate information and select commands to the electronic system. Input devices used with input device interface 1114 include, for example, alphanumeric keyboards and pointing devices (also called "cursor control devices"). Output device interface 1106 enables, for example, the display of images generated by electronic system 1100. Output devices used with output device interface 1106 include, for example, printers and display devices, such as a liquid crystal display (LCD), a light emitting diode (LED) display, an organic light emitting diode (OLED) display, a flexible display, a flat panel display, a solid state display, a projector, or any other device for outputting information.

One or more embodiments may include devices that function as both input and output devices, such as a touchscreen. In these embodiments, feedback provided to the user can be any form of sensory feedback, such as visual feedback, auditory feedback, or tactile feedback; and input from the user can be received in any form, including acoustic, speech, or tactile input.

Finally, as shown in FIG. 11, bus 1108 also couples electronic system 1100 to a network (not shown) through network interface 1116. In this manner, the computer can be a part of a network of computers (such as a local area network ("LAN"), a wide area network ("WAN"), or an Intranet, or a network of networks, such as the Internet. Any or all components of electronic system 1100 can be used in conjunction with the subject disclosure.

Many of the above-described features and applications may be implemented as software processes that are specified as a set of instructions recorded on a computer readable storage medium (alternatively referred to as computer-readable media, machine-readable media, or machine-readable storage media). When these instructions are executed by one or more processing unit(s) (e.g., one or more processors, cores of processors, or other processing units), they cause the processing unit(s) to perform the actions indicated in the instructions. Examples of computer readable media include, but are not limited to, RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, ultra density optical discs, any other optical or magnetic media, and floppy disks. In one or more embodiments, the computer readable media does not include carrier waves and electronic signals passing wirelessly or over wired connections, or any other ephemeral signals. For example, the computer readable media may be entirely restricted to tangible, physical objects that store information in a form that is readable by a computer. In one or more embodiments, the computer readable media is non-transitory computer readable media, computer readable storage media, or non-transitory computer readable storage media.

In one or more embodiments, a computer program product (also known as a program, software, software application, script, or code) can be written in any form of programming language, including compiled or interpreted languages, declarative or procedural languages, and it can be deployed in any form, including as a stand alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

While the above discussion primarily refers to microprocessor or multi-core processors that execute software, one or more embodiments are performed by one or more integrated circuits, such as application specific integrated circuits (ASICs) or field programmable gate arrays (FPGAs). In one or more embodiments, such integrated circuits execute instructions that are stored on the circuit itself.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. Skilled artisans may implement the described functionality in varying ways for each particular application. Various components and blocks may be arranged differently (e.g., arranged in a different order, or partitioned in a different way) all without departing from the scope of the subject technology.

It is understood that any specific order or hierarchy of blocks in the processes disclosed is an illustration of example approaches. Based upon design preferences, it is understood that the specific order or hierarchy of blocks in the processes may be rearranged, or that all illustrated blocks be performed. Any of the blocks may be performed simultaneously. In one or more embodiments, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The predicate words "configured to", "operable to", and "programmed to" do not imply any particular tangible or intangible modification of a subject, but, rather, are intended to be used interchangeably. In one or more embodiments, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as an "aspect" may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such an "embodiment" may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as a "configuration" may refer to one or more configurations and vice versa.

The word "exemplary" is used herein to mean "serving as an example, instance, or illustration." Any embodiment described herein as "exemplary" or as an "example" is not necessarily to be construed as preferred or advantageous over other embodiments. Furthermore, to the extent that the term "include," "have," or the like is used in the description or the claims, such term is intended to be inclusive in a manner similar to the term "comprise" as "comprise" is interpreted when employed as a transitional word in a claim.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but are to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the subject disclosure.

What is claimed is:

1. A system, comprising:
   an infusion device;
   one or more processors; and
   a memory including instructions that, when executed by the one or more processors, cause the one or more processors to:
   receive, based on signals from a user device associated with a user in a healthcare facility, current position data for the user device;
   determine, based on the current position data received for the user device, a location of the user device in the healthcare facility;
   determine, based on the location, that the user associated with the user device has moved within a proximity of the infusion device and within a proximity of a patient in the healthcare facility;
   determine, responsive to determining that the user device has moved within the proximity of the infusion device and the patient, that the infusion device is currently experiencing an error condition regarding an administration of a medication by the infusion device to the patient;
   determine, after determining that the infusion device is currently experiencing an error condition, a corrective action for the error condition;
   automatically cause the user device to display, responsive to determining that the user device has moved within the proximity of the infusion device and the patient and determining that the infusion device is currently experiencing the error condition, a user interface including a notification that the user device is within the proximity of the infusion device and that the infusion device is experiencing the error condition, the user interface including information regarding the corrective action, wherein the user interface automatically changes when the user device moves away from the infusion device; and
   cause, by the automatically displayed user interface based on the determined corrective action and when the user device has moved within the proximity of the infusion device, a reprogramming of the infusion device based on the location and based on a type of the medication or a type of alarm generated by the infusion device to cause an operation of the infusion device to be changed in response to the reprogramming.

2. The system of claim 1, wherein determining that the user device has moved within a proximity of the infusion device comprises a wireless signal being exchanged between the infusion device and the user device, wherein the one or more processors are further caused to:

cause the infusion device to send the notification to the user device.

3. The system of claim 1, wherein determining that the user device has moved within a proximity of the infusion device comprises:
   detecting the user device or the infusion device based on triangulation of wireless signals received from the user device or the infusion device, respectively.

4. The system of claim 1, wherein determining that the user device has moved within a proximity of the patient comprises the user device receiving information wirelessly from a patient identification device.

5. The system of claim 1, wherein the one or more processors are further caused to:
   receive a vital sign of the patient; and
   provide the vital sign for display by the user device with the notification.

6. The system of claim 1, wherein providing the notification comprises:
   selecting an visual alert to be displayed on the infusion device instead of an audible alert based on the user device being located within the proximity of the infusion device.

7. The system of claim 1, wherein the one or more processors are further caused to:
   receive, from each of a plurality of patient information devices, one or more patient identifiers for one or more respective patients located proximate to the patient information device;
   determine a location of a patient information device associated with the patient; and
   determine a location of the patient based on the location of the patient information device.

8. The system of claim 4, wherein the patient identification device configured to be affixed to the patient and is configured to transmit an identifier for the patient based by a radio frequency.

9. The system of claim 1, wherein providing the notification comprises:
   automatically activating a user interface on the user device responsive to determining that the user device moved within the proximity of the infusion device and the patient and determining that the infusion device is currently experiencing the error condition.

10. The system of claim 1, wherein the one or more processors being caused to determine that the user has moved within the proximity of the infusion device and within the proximity of the patient comprises the one or more processors being caused to determine that the user device detected the presence of the infusion device and detected a presence of a patient identification device attached to the patient.

11. A method for detecting and correcting an infusion pump experiencing an error, the method comprising:
   receiving, based on signals from a user device associated with a user in a healthcare facility, current position data for the user device;
   determining, based on the current position data received for the user device, a location of the user device in the healthcare facility;
   determining, based on the location, that a user device has moved within a proximity of an infusion pump and within a proximity of a patient in the healthcare facility;
   determining, responsive to determining that the user device has moved within the proximity of the infusion pump and the patient, that the infusion pump is currently experiencing an error condition regarding an administration of a medication by the infusion pump to the patient;
   determining, after determining that the infusion pump is currently experiencing an error condition, a corrective action for the error condition;
   automatically causing the user device to display, based on determining that the user device has moved within the proximity of the infusion pump and the patient and determining that the infusion pump is currently experiencing the error condition, a user interface including a notification that the user device is within the proximity of the infusion pump and that the infusion pump is experiencing the error condition, the user interface including information regarding the corrective action; and
   causing, by the automatically displayed user interface based on the determined corrective action and when the user device has moved within the proximity of the infusion pump, a reprogramming of, the infusion pump based on the location and based on a type of the medication or a type of alarm generated by the infusion pump to cause an operation of the infusion pump to be changed in response to the reprogramming.

12. The method of claim 11, further comprising:
   receiving a vital sign of the patient; and
   providing the vital sign for display by the user device with the notification.

13. The method of claim 11, wherein determining that the user device has moved within a proximity of the infusion pump comprises a wireless signal being exchanged between the infusion pump and the user device, wherein the method further comprises:
   the infusion pump sending the notification to the user device.

14. The method of claim 11, wherein determining that the user device has moved within a proximity of the infusion pump comprises:
   detecting the user device or the infusion pump based on triangulation of wireless signals received from the user device or the infusion pump, respectively.

15. The method of claim 11, wherein determining that the user device has moved within a proximity of the patient comprises the user device receiving information wirelessly from a patient identification device.

16. The method of claim 11, wherein providing the notification comprises:
   selecting an visual alert to be displayed on the infusion pump instead of an audible alert based on the user device being located within the proximity of the infusion pump.

17. The method of claim 11, further comprising:
   receiving, from each of a plurality of patient information devices, one or more patient identifiers for one or more respective patients located proximate to the patient information device;
   determining a location of a patient information device associated with the patient; and
   determining a location of the patient based on the location of the patient information device.

18. The method of claim 15, wherein the patient identification device is affixed to the patient and is configured to transmit an identifier for the patient based by radio frequency.

19. The method of claim 11, wherein determining that the user has moved within the proximity of the infusion pump and within the proximity of the patient comprises determining that the user device detected a presence of the infusion pump and detected a presence of a patient identification device attached to the patient.

20. A non-transitory machine-readable medium having instructions stored thereon that, when executed by a machine, cause the machine to perform a method for detecting and correcting an infusion device experiencing an error, the method comprising:

receiving, based on signals from a user device associated with a user in a healthcare facility, current position data for the user device;

determining, based on the current position data received for the user device, a location of the user device in the healthcare facility;

determining, based on the location, that a user device has moved within a proximity of an infusion device and within a proximity of a patient in the healthcare facility;

determining, responsive to determining that the user device has moved within the proximity of the infusion device and the patient, that the infusion device is currently experiencing an error condition regarding an administration of medication by the infusion device to the patient;

determining, after determining that the infusion device is currently experiencing an error condition, a corrective action for the error condition;

automatically causing the user device to display, based on determining that the user device has moved within the proximity of the infusion device and the patient and determining the infusion device is currently experiencing the error condition, a user interface including a notification that the user device is within the proximity of the infusion device and that the infusion device is experiencing the error condition, the user interface including information regarding the corrective action; and causing, by the automatically displayed user interface based on the determined corrective action, and when the user device has moved within the proximity of the infusion device, a reprogramming of the infusion device based on the location and based on a type of the medication or a type of alarm generated by the infusion device to cause an operation of the infusion device to be changed in response to the reprogramming.

* * * * *